US012072331B2

(12) United States Patent
Jollez

(10) Patent No.: US 12,072,331 B2
(45) Date of Patent: *Aug. 27, 2024

(54) CHROMOGENIC ABSORBENT MATERIAL FOR ANIMAL LITTER

(71) Applicant: 7905122 CANADA INC., Quebec (CA)

(72) Inventor: Paul Jollez, Quebec (CA)

(73) Assignee: 7905122 CANADA INC., Boucherville (CA)

( * ) Notice: Subject to any disclaimer, the term of this patent is extended or adjusted under 35 U.S.C. 154(b) by 738 days.

This patent is subject to a terminal disclaimer.

(21) Appl. No.: 17/153,425

(22) Filed: Jan. 20, 2021

(65) Prior Publication Data

US 2021/0140950 A1    May 13, 2021

Related U.S. Application Data

(63) Continuation of application No. 16/202,225, filed on Nov. 28, 2018, now Pat. No. 10,908,150, which is a continuation of application No. 15/121,936, filed as application No. PCT/CA2014/050140 on Feb. 27, 2014, now Pat. No. 10,175,231.

(51) Int. Cl.
| | | |
|---|---|---|
| *G01N 33/52* | (2006.01) | |
| *A01K 1/015* | (2006.01) | |
| *B01J 20/24* | (2006.01) | |
| *B01J 20/28* | (2006.01) | |
| *C12Q 1/54* | (2006.01) | |

(52) U.S. Cl.
CPC ........... *G01N 33/52* (2013.01); *A01K 1/0152* (2013.01); *A01K 1/0155* (2013.01); *B01J 20/24* (2013.01); *B01J 20/28004* (2013.01); *B01J 20/28011* (2013.01); *B01J 20/28069* (2013.01); *B01J 20/28073* (2013.01); *B01J 20/28076* (2013.01); *C12Q 1/54* (2013.01); *C12Y 101/03004* (2013.01); *C12Y 111/01007* (2013.01); *B01J 2220/445* (2013.01); *B01J 2220/4825* (2013.01); *B01J 2220/49* (2013.01); *B01J 2220/68* (2013.01); *G01N 2333/904* (2013.01); *G01N 2333/908* (2013.01)

(58) Field of Classification Search
None
See application file for complete search history.

(56) References Cited

U.S. PATENT DOCUMENTS

| | | |
|---|---|---|
| 4,460,684 A | 7/1984 | Bauer |
| 4,615,923 A | 10/1986 | Marx |
| 4,883,021 A | 11/1989 | Ducharme et al. |
| 5,183,742 A * | 2/1993 | Omoto ............... C12Q 1/28 435/14 |
| 5,735,232 A | 4/1998 | Lang et al. |
| 5,760,121 A | 6/1998 | Beall et al. |
| 6,019,062 A | 2/2000 | Lombard et al. |
| 6,039,004 A | 3/2000 | Robert et al. |
| 6,042,839 A | 3/2000 | Lahanas et al. |
| 6,197,849 B1 | 3/2001 | Zilg et al. |
| 6,220,206 B1 | 4/2001 | Sotillo et al. |
| 6,228,903 B1 | 5/2001 | Beall et al. |
| 6,261,640 B1 | 7/2001 | Pinnavaia et al. |
| 6,271,297 B1 | 8/2001 | Ishida |
| 6,376,034 B1 | 4/2002 | Brander |
| 6,399,690 B2 | 6/2002 | Lan et al. |
| 6,407,155 B1 | 6/2002 | Qian et al. |
| 6,414,069 B1 | 7/2002 | Pinnavaia et al. |
| 6,521,690 B1 | 2/2003 | Ross et al. |
| 6,579,927 B1 | 6/2003 | Fischer |
| 6,586,500 B2 | 7/2003 | Bagrodia et al. |
| 6,730,719 B2 | 5/2004 | Powell |
| 7,533,630 B2 | 5/2009 | Steckel et al. |
| 9,547,000 B2 | 1/2017 | Gravel-Lacroix et al. |
| 2002/0165305 A1 | 11/2002 | Knudson et al. |
| 2002/0169246 A1 | 11/2002 | Barbee et al. |

(Continued)

FOREIGN PATENT DOCUMENTS

| | | |
|---|---|---|
| CA | 2308537 A1 | 11/2000 |
| CA | 2352502 A1 | 1/2002 |

(Continued)

OTHER PUBLICATIONS

Masuda et al. ("Superabsorbent Polymers", In: Encyclopedia of Polymeric Nanomaterials; Kobayashi, S., Müllen, K. (eds); Springer: Berlin, Heidelberg; e-published: Jan. 2014; pp. 1-18). (Year: 2014).*
Chenu, et al., "Modifications de l'organisation texturale d'une montmorillonite calcique liées a l'adsorption d'un polysaccharide", Comptes Rendus de I'Académie des Sciences, 1990, t. 310, Série II, pp. 975-980.
Darder, et al., "Biopolymer-Clay Nanocomposites Based on Chitosan Intercallated in Montmorillonite", Chemistry of Materials, 2003, 15(20), pp. 3774-3780.
DeCarvalho, et al., "A first insight on composites of thermoplastic starch and kaolin", Carbohydrate Polymers, 2001, vol. 45(2), pp. 189-194.

(Continued)

*Primary Examiner* — Michelle F. Paguio Frising
(74) *Attorney, Agent, or Firm* — AVEK IP, LLC

(57) ABSTRACT

A chromogenic absorbent material for an animal litter includes an oxidizing agent responsive to peroxidatic/pseudoperoxidatic activity in an animal excretion or a first catalytic compound generating the oxidizing agent in situ. The material also includes a chromogenic indicator being chromogenically responsive to the oxidizing activity of the oxidizing agent, and an absorptive material which is porous, for absorbing the animal excretion. The absorptive material includes a water-absorbing polysaccharide providing absorptive properties to the chromogenic absorbent material; and may also include a second polysaccharide and a superabsorbent polymer. The material may be obtained in the form of particles having a low density and a high porosity, and is usable in conjunction with an animal litter for detecting various diseases in animals.

22 Claims, 15 Drawing Sheets

(56) References Cited

U.S. PATENT DOCUMENTS

| | | |
|---|---|---|
| 2003/0060555 A1 | 3/2003 | Lorah et al. |
| 2003/0134942 A1 | 7/2003 | Lee et al. |
| 2003/0170905 A1 | 9/2003 | Kamyshny et al. |
| 2008/0022940 A1 | 1/2008 | Kirsch et al. |
| 2014/0000525 A1 | 1/2014 | Schumski et al. |

FOREIGN PATENT DOCUMENTS

| | | |
|---|---|---|
| CA | 2462053 A1 | 9/2004 |
| CA | 2607676 A1 | 5/2008 |
| CA | 2607753 A1 | 5/2008 |
| CA | 2607758 A1 | 5/2008 |
| CA | 2737489 A1 | 11/2010 |
| DE | 202013005052 U1 | 2/2014 |
| DE | 6020100148629 | 6/2014 |
| EP | 1203789 A1 | 5/2002 |
| EP | 1327435 A1 | 7/2003 |
| FR | 2303290 A1 | 10/1976 |
| GB | 1240884 A | 7/1971 |
| JP | 2001296933 A1 | 10/2001 |
| JP | 2002203936 A | 7/2002 |
| JP | 2009187493 A1 | 8/2009 |
| JP | 2009265086 A | 11/2009 |
| WO | 9858533 A1 | 12/1998 |
| WO | 2004043663 A2 | 5/2004 |
| WO | 2010133001 A1 | 11/2010 |

OTHER PUBLICATIONS

Li, et al., "A new hybrid nanocomposite prepared by graft copolymerization of butyl acrylate onto chitosan in the presence of organophilic montmorillonite", Radiation Physics and Chemistry, 2004, 69(6) APR, pp. 467-471.

McGlashan, S.A. et al., "Preparation and characterisation of biodegradable starch-based nanocomposite materials" Polymer International, 2003, 52(11), pp. 1767-1773.

Okada, et al., Mat. Res. Soc. Proc., 1990, 171, 45-50.

Park, et al., "Preparation and Properties of Biodegradable Thermoplastic Starch/Clay Hybrids", Macromolecular Macromolecular Materials and Engineering, 2002, 287(8), pp. 553-558.

Reis, et al., "Structure Development and Control of Injection-Molded Hydroxylapatite-Reinforced Starch EVOH composites", J. Advances in Polymer Technology, 1997, vol. 16, pp. 263-277.

Zhang, S et al., "β-Cyclodextrin sensitized chemiluminescence of hemoglobin-hydrogen-carbonate and its analytical application", Analytica Chimica Acta, Jan. 3, 2003, vol. 475, No. 1-2, pp. 163 to 170.

International search report for PCT/CA2014/050140, dated Oct. 31, 2014.

\* cited by examiner 30 mins after contact 2h after contact 18h after contact 30 mins after contact 2h after contact 18h after contact

CHROMOGENIC ABSORBENT MATERIAL FOR ANIMAL LITTER

CROSS REFERENCE TO RELATED APPLICATIONS

This application is a continuation of U.S. patent application Ser. No. 16/202,225, filed on Nov. 28, 2018, which is a continuation of U.S. patent application Ser. No. 15/121,936, filed on Aug. 26, 2016, which is a National Stage application of International Application No. PCT/CA2014/050140, filed Feb. 27, 2014, each of which is incorporated by reference herein in their entirety.

FIELD

The technical field relates to animal disease detection and chromogenic materials, and more particularly to animal litter including chromogenic absorbent material for detecting animal diseases.

BACKGROUND

Domestic animals such as cats are susceptible to various diseases, ailments and conditions, which are not only arduous and painful for the animal itself but also a source of concern and stress for animal owners. While animal owners nurture, watch over and bestow affection on their pets, they must balance this attention with other responsibilities. Convenience is thus an important factor when taking care of a domestic animal. While owners may be devoted and considerate to their pets, they may lack the sophistication to diagnose animal diseases, ailments and conditions. Convenient, simple and effective means to inform pet owners of the presence of diseases, such as urinary infections, are desired so that appropriate steps can be taken to reverse, mitigate or avoid serious illness in the animal.

For example, feline urinary tract disease can be a serious condition for cats. In feline urinary tract disease, crystals of magnesium ammonium phosphate can precipitate in the cat's urinary tract and cause obstruction. If untreated, the obstruction can lead to intense pain and can often be fatal within days. In some cases, upon observing feline urinary tract disease symptoms—such as bloody urine and urination discomfort and straining—cat owners often consult their veterinarian who may be able to provide treatments, which may be expensive. However, many cats with feline urinary tract disease do not show any obvious symptoms, which is why this disease has been referred to as a "silent killer".

Another example of a serious condition for cats is diabetes. Diabetes strikes about 1 in 400 cats and has become increasingly common. Symptoms of diabetes in cats are similar to those in humans, and about 80% to 95% of diabetic cats experience something similar to type-2 diabetes in humans. Cats suffering of diabetes usually become severely insulin-dependent by the time symptoms are diagnosed. In cats suffering from type-2 diabetes, early treatment can sometimes lead to diabetic remission, in which the cat no longer needs injected insulin. If left untreated, the condition leads to increasingly weak cats, malnutrition, ketoacidosis and/or dehydration, and eventually death.

Early detection of diseases such as feline urinary tract disease or diabetes is therefore of paramount importance in facilitating treatment, lessening the likelihood of severe complications or aggravations, and reducing the cost of treatment.

Some methods of early detection are known. Early detection may be possible by occult blood testing, allowing animal owners to treat the problems of urinary tract disease or diabetes by changing the animals' diets or by seeking the help of a veterinarian. However, some known occult blood or glucose testing techniques present various disadvantages concerning the complexity and inconvenience of the tests. For instance, animals will often resist urine sample gathering.

It is known to use diagnostic agents, incorporated into test strips, beads or particles, for detection purposes. Usually, such test strips consist of an absorbent carrier made from fibrous or non-woven material, in the simplest case filter paper, which is coated or impregnated with the detection reagents. Components of the detection reagent may be a chromogenic compound as an indicator, an oxidizing agent such as a hydroperoxide as an oxidizer of the indicator. The oxidizing agent is sometimes also called a sensitizer or an accelerator. Standard additional components are, apart from a surface-active agent (wetting agent), thickening agents which prevent the bleeding of the wetted test field, pigments, complex-forming agents and/or other stabilizers for the chromogen and/or the hydroperoxide.

Similarly, various analytical methods are presently available for detecting the presence of "peroxidatively active substances" in samples such as urine, fecal suspensions, and gastrointestinal contents. According to U.S. Pat. No. 4,460,684, hemoglobin and its derivatives are typical of such peroxidatively active substances because they behave in a manner similar to the enzyme peroxidase. Such substances are also referred to as pseudoperoxidases. Peroxidatively active substances are enzyme-like in that they catalyze the redox reaction between peroxides and benzidine, o-tolidine, 3,3',5,5'-tetramethylbenzidine, 2,7-diaminofluorene or similar benzidine-type indicator substances, thereby producing a detectable response such as a color change. For example, most methods for determining the presence of occult blood in test samples rely on this pseudoperoxidatic activity. A benzidine-type indicator responds in the presence of hydroperoxide and/or peroxidase by changing its light absorptive capability.

Providing a reliable occult blood or glucose detection system in animal litter itself also has many problems and challenges. For example, the test indicator material should be stable when exposed to a wide variety of ambient conditions, be they dry or humid, and over a wide range of temperatures. Such stability is quite often difficult to achieve.

A further problem with many known test indicators is that pet owners are insufficiently observant or sophisticated to appreciate the positive indication, such as a color change, before the indicator decays. Many known indicators do not stay at the changed color for a sufficient period of time to allow pet owners to reliably recognize the indicated health issue.

An additional problem with various detection reagents mixed with animal litter is that the test reagents give off sufficient scent such that cats, which have an extraordinary sense of smell, recognize the odor change in their litter and thus tend to shy away from the litter. As will be appreciated, this not only defeats the purpose of a convenient detector but can also cause unwanted excretory mishaps. Thus, test reagents with significant, offensive or upsetting odors—both to the user and the cat—have many disadvantages.

A further problem with known detection reagents is poor shelf life stability, particularly if combined with an animal litter for storage as a single mixture. Poor stability leads to disadvantages in the ability to store, transport, display, purchase and use the detection-litter combination.

Detection materials that are merely coated over the surface of a carrier material also have various disadvantages that may relate to poor shelf-life stability, low in-use stability and lifetime, and insufficient color change visibility.

Known materials and methods for detection of feline urinary tract disease or diabetes have involved one or more of the above deficiencies.

Some detection methods are disclosed in WO 2010133001 (Jollez et al.) which describes a chromogenic composite material for use with animal litter. The composite material can include an absorptive polymer material; clay; a chromogenic indicator; and an oxidizing agent that is available and responsive to peroxidase or pseudoperoxidase activity in the feline urine to activate the chromogenic indicator. The chromogenic indicator may be 3,3',5,5'-tetramethylbenzidine, also referred to as TMB.

Despite the developments in detection methods for animal excretion tract disease, there is still a need for an improved technology.

SUMMARY

A chromogenic absorbent material is described herein for detecting substances in animal excretions.

In some implementations, there is provided a chromogenic absorbent material for an animal litter, comprising:
an oxidizing agent responsive to peroxidatic/pseudoperoxidatic activity in an animal excretion to provide oxidizing activity;
a chromogenic indicator being chromogenically responsive to the oxidizing activity of the oxidizing agent; and
an absorptive material which is porous, for absorbing the animal excretion, the absorptive material comprising:
a water-absorbing polysaccharide providing absorptive properties to the chromogenic absorbent material; and
a second polysaccharide providing structural integrity to the chromogenic absorbent material.

In some implementations, the second polysaccharide comprises a crystalline polysaccharide.

In some implementations, the crystalline polysaccharide comprises cellulose, a cellulose derivative or mixtures thereof.

In some implementations, the cellulose comprises microcrystalline cellulose (MCC), nanocrystalline cellulose (NCC), or a mixture thereof.

In some implementations, the absorptive material comprises:
about 35 wt. % to about 65 wt. % of the water-absorbing polysaccharide; and
about 35 wt. % to about 65 wt. % of the second polysaccharide.

In some implementations, the absorptive material comprises:
about 45 wt. % to about 55 wt. % of the water-absorbing polysaccharide; and
about 45 wt. % to about 55 wt. % of the second polysaccharide.

In some implementations, there is provided a chromogenic absorbent material for an animal litter, comprising:
an oxidizing agent responsive to peroxidatic/pseudoperoxidatic activity in an animal excretion to provide oxidizing activity;
a chromogenic indicator being chromogenically responsive to the oxidizing activity of the oxidizing agent; and
an absorptive material which is porous, for absorbing the animal excretion, the absorptive material comprising a water-absorbing polysaccharide,
wherein the chromogenic absorbent material has a density of about 0.20 g/cm$^3$ to about 0.39 g/cm$^3$.

In some implementations, the density of the chromogenic absorbent material is about 0.25 g/cm$^3$ to about 0.35 g/cm$^3$.

In some implementations, the density of the chromogenic absorbent material is about 0.30 g/cm$^3$ to about 0.35 g/cm$^3$.

In some implementations, there is provided a chromogenic absorbent material for an animal litter, comprising:
an oxidizing agent responsive to peroxidatic/pseudoperoxidatic activity in an animal excretion to provide oxidizing activity;
a chromogenic indicator being chromogenically responsive to the oxidizing activity of the oxidizing agent; and
an absorptive material which is porous, for absorbing the animal excretion, the absorptive material comprising a water-absorbing polysaccharide,
wherein the chromogenic absorbent material is a porous material having an effective porosity of about 0.5 mL/g to about 2.0 mL/g.

In some implementations, the effective porosity is of about 0.6 mL/g to about 1.5 mL/g.

In some implementations, the effective porosity is of about 0.8 mL/g to about 1.2 mL/g.

In some implementations, the effective porosity is of about 0.9 mL/g to about 1.1 mL/g.

In some implementations, the chromogenic absorbent material is provided with pores having an equivalent diameter greater than about 20 μm.

In some implementations, the chromogenic absorbent material is provided with pores having an equivalent diameter of about 20 μm to about 40 μm.

In some implementations, the chromogenic absorbent material is provided with pores having an equivalent diameter of about 20 μm to about 30 μm.

In some implementations, the chromogenic absorbent material has a free swelling capacity greater than about 900%.

In some implementations, the chromogenic absorbent material has a free swelling capacity greater than about 1000%.

In some implementations, there is provided a chromogenic absorbent material for an animal litter, comprising:
an oxidizing agent responsive to peroxidatic/pseudoperoxidatic activity in an animal excretion to provide oxidizing activity;
a chromogenic indicator being chromogenically responsive to the oxidizing activity of the oxidizing agent; and
an absorptive material which is porous, for absorbing the animal excretion, the absorptive material comprising:
a water-absorbing polysaccharide providing absorptive properties to the chromogenic absorbent material; and
a superabsorbent polymer (SAP).

In some implementations, the absorptive material comprises up to about 3 wt. % of the SAP.

In some implementations, the absorptive material comprises about 1 wt. % to about 3 wt. % of the SAP.

In some implementations, the absorptive material comprises about 1 wt. % to about 2 wt. % of the SAP.

In some implementations, the SAP comprises at least one of a poly(acrylic acid) and a poly(methacrylic acid), or a salt thereof.

In some implementations, there is provided a chromogenic absorbent material for an animal litter, comprising:

an oxidizing agent responsive to peroxidatic/pseudoperoxidatic activity in an animal excretion to provide oxidizing activity;
a chromogenic indicator being chromogenically responsive to the oxidizing activity of the oxidizing agent; and
an absorptive material which is porous, for absorbing the animal excretion, the absorptive material comprising:
  a water-absorbing polysaccharide providing absorptive properties to the chromogenic absorbent material; and
  a second polysaccharide providing structural integrity to the chromogenic absorbent material,
wherein the chromogenic absorbent material is a porous material having:
  an effective porosity of about 0.5 mL/g to about 2.0 mL/g; and
  a density of about 0.20 g/cm$^3$ to about 0.39 g/cm$^3$.

In some implementations, the water-absorbing polysaccharide comprises a starch, a modified starch, a cellulose derivative or a gelling polysaccharide, or a mixture thereof.

In some implementations, the water-absorbing polysaccharide comprises pregelatinized starch.

In some implementations, the cellulose derivative comprises a cellulose ester or a cellulose ether, or a mixture thereof.

In some implementations, the cellulose derivative comprises carboxymethyl cellulose (CMC).

In some implementations, the gelling polysaccharide comprises agar-agar, guar or xanthan, or a mixture thereof.

In some implementations, the oxidizing agent comprises a hydroperoxide or a hydroperoxide precursor, or a combination thereof.

In some implementations, the hydroperoxide comprises hydrogen peroxide, cumene hydroperoxide or diisopropylbenzene dihydroperoxide, or a combination thereof.

In some implementations, the oxidizing agent and the chromogenic indicator are distributed within the absorptive material.

In some implementations, the chromogenic indicator comprises a benzidine-type compound.

In some implementations, the benzidine-type compound comprises 3,3',5,5'-tetramethylbenzidine.

In some implementations, the chromogenic absorbent material further comprises a buffering agent, a stabilizer, a metal scavenger agent or a color enhancer or a combination thereof.

In some implementations, the color enhancer comprises 6-methoxyquinoline, lepidin, phenol derivatives, nitrobenzene, N-methylpyrrolidone or ethylene carbonate or a combination thereof.

In some implementations, the buffering agent comprises citrate, sodium citrate, phosphate or acetate or a combination thereof.

In some implementations, the stabilizer comprises ammonium molybdate, polyethylene glycol, polyvinylpyrrolidone, polyethylene oxide or derivatives thereof or a combination thereof.

In some implementations, the metal-scavenger agent comprises ethylenediaminetetraacetic acid (EDTA) or EDTA sodium salt or a combination thereof.

In some implementations, the chromogenic indicator is responsive to the oxidizing agent by turning blue in presence of the peroxidatic/pseudoperoxidatic activity in the animal excretions.

In some implementations, the chromogenic absorbent material turns to blue in presence of the peroxidatic/pseudoperoxidatic activity after a contact time with the animal excretion between about 10 seconds and about 30 min.

In some implementations, the chromogenic absorbent material turns to blue in presence of the peroxidatic/pseudoperoxidatic activity after a contact time with the animal excretion between about 10 seconds and about 1 min.

In some implementations, there is provided a chromogenic absorbent material for an animal litter, comprising:
  a first catalytic compound for in situ generation of an oxidizing agent responsive to peroxidatic/pseudoperoxidatic activity in an animal excretion, the oxidizing agent providing oxidizing activity;
  a chromogenic indicator being chromogenically responsive to the oxidizing activity of the oxidizing agent;
  a second catalytic compound for catalyzing the oxidation of the chromogenic indicator upon in situ generation of the oxidizing agent; and
  an absorptive material which is porous, for absorbing the animal excretion, the absorptive material comprising:
    a water-absorbing polysaccharide providing absorptive properties to the chromogenic absorbent material; and
    a second polysaccharide providing structural integrity to the chromogenic absorbent material.

In some implementations, there is provided a chromogenic absorbent material for an animal litter, comprising:
  a first catalytic compound for in situ generation of an oxidizing agent responsive to peroxidatic/pseudoperoxidatic activity in an animal excretion, the oxidizing agent providing oxidizing activity;
  a chromogenic indicator being chromogenically responsive to the oxidizing activity of the oxidizing agent;
  a second catalytic compound for catalyzing the oxidation of the chromogenic indicator upon in situ generation of the oxidizing agent; and
  an absorptive material for absorbing the animal excretion, the absorptive material comprising a water-absorbing polysaccharide,
  wherein the chromogenic absorbent material has a density of about 0.20 g/cm$^3$ to about 0.39 g/cm$^3$.

In some implementations, there is provided a chromogenic absorbent material for an animal litter, comprising:
  a first catalytic compound for in situ generation of an oxidizing agent responsive to peroxidatic/pseudoperoxidatic activity in an animal excretion, the oxidizing agent providing oxidizing activity;
  a chromogenic indicator being chromogenically responsive to the oxidizing activity of the oxidizing agent;
  a second catalytic compound for catalyzing the oxidation of the chromogenic indicator upon in situ generation of the oxidizing agent; and
  an absorptive material for absorbing the animal excretion, the absorptive material comprising a water-absorbing polysaccharide,
  wherein the chromogenic absorbent material is a porous material having an effective porosity of about 0.5 mL/g to about 2.0 mL/g.

In some implementations, there is provided a chromogenic absorbent material for an animal litter, comprising:
  a first catalytic compound for in situ generation of an oxidizing agent responsive to peroxidatic/pseudoperoxidatic activity in an animal excretion, the oxidizing agent providing oxidizing activity;
  a chromogenic indicator being chromogenically responsive to the oxidizing activity of the oxidizing agent;

a second catalytic compound for catalyzing the oxidation of the chromogenic indicator upon in situ generation of the oxidizing agent; and
an absorptive material which is porous, for absorbing the animal excretion, the absorptive material comprising:
a water-absorbing polysaccharide providing absorptive properties to the chromogenic absorbent material; and
a superabsorbent polymer (SAP).

In some implementations, there is provided a chromogenic absorbent material for an animal litter, comprising:
a first catalytic compound for in situ generation of an oxidizing agent responsive to peroxidatic/pseudoperoxidatic activity in an animal excretion, the oxidizing agent providing oxidizing activity;
a chromogenic indicator being chromogenically responsive to the oxidizing activity of the oxidizing agent;
a second catalytic compound for catalyzing the oxidation of the chromogenic indicator upon in situ generation of the oxidizing agent; and
an absorptive material which is porous, for absorbing the animal excretion, the absorptive material comprising:
a water-absorbing polysaccharide providing absorptive properties to the chromogenic absorbent material; and
a second polysaccharide providing structural integrity to the chromogenic absorbent material,
wherein the chromogenic absorbent material is a porous material having:
an effective porosity of about 0.5 mL/g to about 2.0 mL/g; and
a density of about 0.20 g/cm$^3$ to about 0.39 g/cm$^3$.

In some implementations, the water-absorbing polysaccharide comprises a cellulose derivative or a gelling polysaccharide, or a mixture thereof.

In some implementations, the first catalytic compound comprises an oxido-reductase enzyme.

In some implementations, the oxido-reductase comprises glucose oxidase (GOx).

In some implementations, the oxidizing agent generated in situ is hydrogen peroxide.

In some implementations, the second catalytic compound comprises a peroxidase, a pseudoperoxidase, or a mixture thereof.

In some implementations, the peroxidase comprises horseradish peroxidase (HRP).

In some implementations, the first catalytic compound, the second catalytic compound and the chromogenic indicator are distributed within the absorptive material.

In some implementations, there is provided a chromogenic absorbent material for detecting a detectable substance in an animal excretion, the chromogenic absorbent material comprising:
a trigger agent;
a chromogenic indicator oxidizable into a colored and/or fluorescent substance in the presence of the trigger agent and the detectable substance; and
an absorptive material which is porous, for absorbing the animal excretion, the absorptive material comprising:
a water-absorbing polysaccharide providing absorptive properties to the chromogenic absorbent material; and
a second polysaccharide providing structural integrity to the chromogenic absorbent material.

In some implementations, there is provided a chromogenic absorbent material for detecting a detectable substance in an animal excretion, the chromogenic absorbent material comprising:
a trigger agent;
a chromogenic indicator oxidizable into a colored and/or fluorescent substance in the presence of the trigger agent and the detectable substance; and
an absorptive material which is porous, for absorbing the animal excretion, the absorptive material comprising:
a water-absorbing polysaccharide providing absorptive properties to the chromogenic absorbent material,
wherein the chromogenic absorbent material has a density of about 0.20 g/cm$^3$ to about 0.39 g/cm$^3$.

In some implementations, there is provided a chromogenic absorbent material for detecting a detectable substance in an animal excretion, the chromogenic absorbent material comprising:
a trigger agent;
a chromogenic indicator oxidizable into a colored and/or fluorescent substance in the presence of the trigger agent and the detectable substance; and
an absorptive material which is porous, for absorbing the animal excretion, the absorptive material comprising:
a water-absorbing polysaccharide providing absorptive properties to the chromogenic absorbent material,
wherein the chromogenic absorbent material is a porous material having an effective porosity of about 0.5 mL/g to about 2.0 mL/g.

In some implementations, there is provided a chromogenic absorbent material for detecting a detectable substance in an animal excretion, the chromogenic absorbent material comprising:
a trigger agent;
a chromogenic indicator oxidizable into a colored and/or fluorescent substance in the presence of the trigger agent and the detectable substance; and
an absorptive material which is porous, for absorbing the animal excretion, the absorptive material comprising:
a water-absorbing polysaccharide providing absorptive properties to the chromogenic absorbent material; and
a superabsorbent polymer (SAP).

In some implementations, there is provided the use of the chromogenic absorbent material as chromogenic particles in combination with animal litter.

In some implementations, the animal litter comprises clay based particles, cellulosic particles, perlite based particles, silica based particles, corn based particles, paper based particles or wheat based particles or a combination thereof.

In some implementations, the clay based particles comprise montmorillonite.

In some implementations, the clay based particles comprise bentonite.

In some implementations, the chromogenic absorbent material is used for detecting blood in animal excretions.

In some implementations, the chromogenic absorbent material is used for detecting glucose in animal excretions.

In some implementations, the chromogenic particles are substantially evenly distributed on a top surface of the animal litter.

In some implementations, the chromogenic particles are substantially evenly distributed within the animal litter.

In some implementations, the chromogenic particles comprise pellets, granules, disks, squares according to their process of manufacture.

In some implementations, there is provided a chromogenic absorbent material for detecting a detectable substance in an animal excretion, the chromogenic absorbent material comprising:
    a trigger agent;
    a chromogenic indicator convertable into a colored and/or fluorescent substance in the presence of the trigger agent and the detectable substance; and
    an absorptive material for absorbing the animal excretion, the absorptive material having a porous and a block-shaped microstructure.

DETAILED DESCRIPTION

Figure 1:
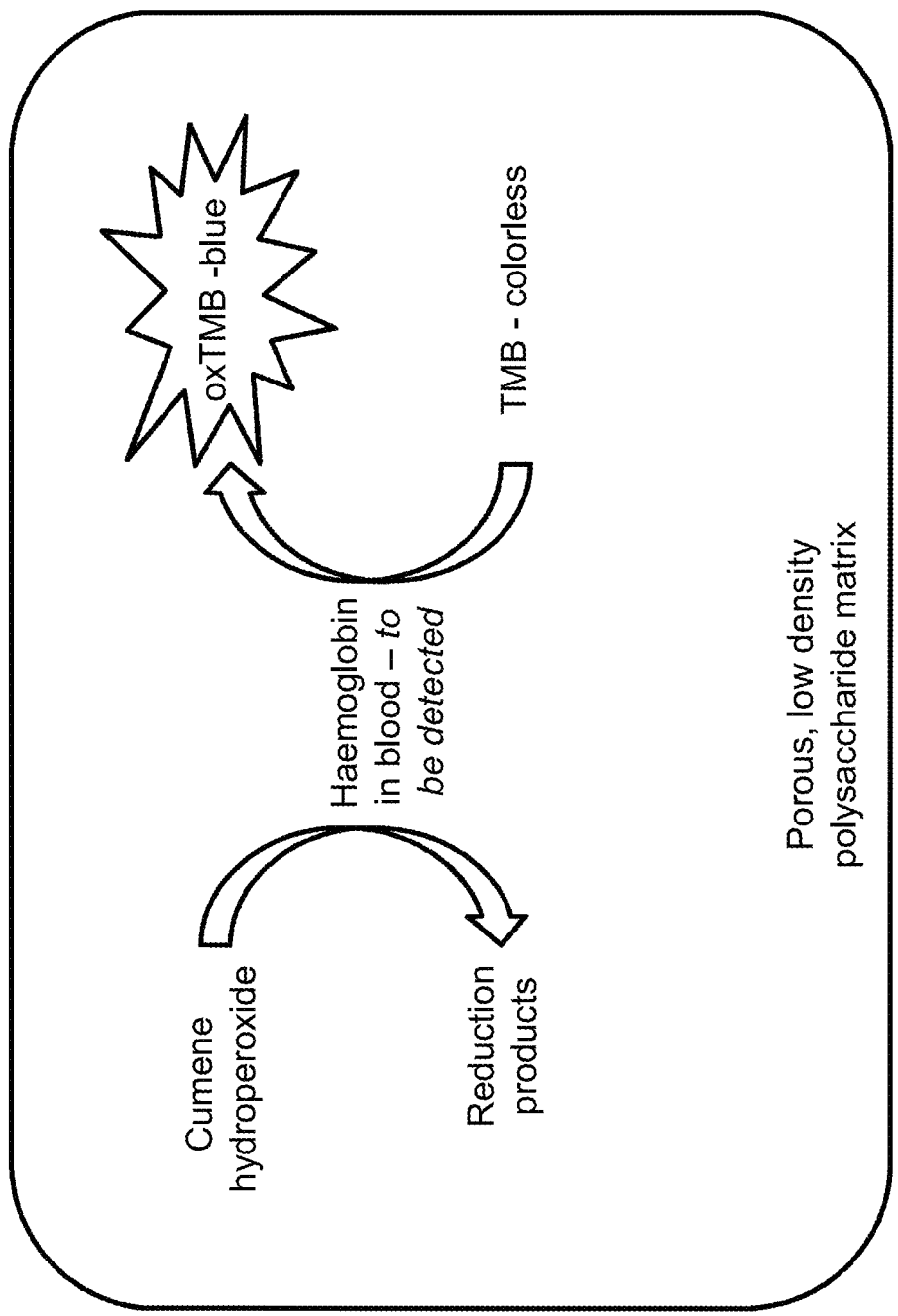
FIG. 1 is a scheme of the reaction pathway taking place in the particles of chromogenic absorbent material for the detection of blood in animal excretions.

A chromogenic absorbent material may include an oxidizing agent, a chromogenic indicator and an absorptive material, for detecting disease features when contacted with animal excretions. In some implementations, the absorptive material includes a water-absorbing polysaccharide and optionally a second crystalline polysaccharide and/or a superabsorbent polymer, and may also have high-porosity and low-density properties.

In some implementations, the chromogenic absorbent material is provided for detecting blood or glucose in excretions. More particularly, the chromogenic absorbent material may be used in connection with an animal litter. Processes for making chromogenic absorbent materials are also described.

It should be understood that excretion refers to any matter excreted by an animal, such as urine or fecal matter. The chromogenic absorbent material may be used in any domestic animal litter including cat litter, dog litter and rodent litter. It may also be used for horse litter, cow litter or any other livestock litter. However, various implementations of the chromogenic absorbent material are not limited to detecting blood or glucose in animal excretions and may be used to detect blood or glucose in human excretions, for example.

Particles of the chromogenic absorbent material may be dispersed within the animal litter or at the surface of the animal litter. The animal litter may include clay based particles, cellulosic particles, perlite based particles, silica based particles, corn based particles, paper based particles, wheat based particles or other organic-based litter particles, or a combination thereof. For example and without being limitative, clay based particles may include bentonite and/or montmorillonite.

In some implementations, the particles of chromogenic absorbent material include: an oxidizing agent responsive to peroxidatic/pseudoperoxidatic activity in an animal excretion to provide oxidizing activity, or a first catalytic compound generating the oxidizing agent in situ; a chromogenic indicator being chromogenically responsive to the oxidizing activity of the oxidizing agent; and an absorptive material for absorbing the animal excretion, the absorptive material including a water-absorbing polysaccharide providing absorptive properties to the chromogenic absorbent material.

In some implementations, the oxidizing agent and/or the first catalytic compound, and the chromogenic indicator are distributed on at least an exterior surface of the absorptive material. In some implementations, the oxidizing agent and/or the first catalytic compound, and the chromogenic indicator are distributed within the absorptive material.

It should be understood that the expression "peroxidatic activity" refers to the ability of catalytic compounds to drive the reaction between hydroperoxides and colorless chromogenic electron donors which become fluorescent or visibly colored after oxidation.

It should be understood that the expression "pseudoperoxidatic activity" refers to the ability of a peroxidase or a non-peroxidase catalytic compound to drive the reaction between hydroperoxidases and colorless chromogenic electron donors which become fluorescent or visibly colored after oxidation. Certain transition metals and their ions and hemoproteins are known to have pseudoperoxidatic activity. Basophils, neutrophils, eosinophils and mast cells synthesize endogenous peroxidase which can be visualized at the ultrastructural level in the secretory apparatus of immature cells. Red blood cells and hematin containing compounds have iron as part of their heme groups, which can catalyze the oxidation of chromogenic electron donors. This pseudoperoxidatic activity can be inhibited with strong $H_2O_2$ solutions, sodium azide and methanol-$H_2O_2$ solutions.

It should be understood that "particle" refers to any pellet, granule or piece of various shapes. Optionally, the particles may generally have a circular cross-section with an average diameter ranging from 2.5 mm to 10 mm. Optionally, the particles may generally have a square or rectangular cross-section with an average length ranging from 5 mm to 20 mm. Optionally, the particles may have a top surface ranging from 19 $mm^2$ to 400 $mm^2$ and a thickness ranging from 1 to 10 mm. The shape(s) of the particles may be conferred by their process of manufacture.

The oxidizing agent is reactive to peroxidatic/pseudoperoxidatic activity and is able to oxidize the chromogenic indicator in the presence of a peroxidase or a pseudoperoxidase. For example, the peroxidase can be horseradish peroxidase. For example, the pseudoperoxidase can be haemoglobin present in blood. In an optional aspect, the oxidizing agent includes a hydroperoxide.

It should be understood that "hydroperoxide" refers to compounds of the general formula ROOH, wherein the R group is an aryl, alkyl or acyl group (organic hydroperoxide), or a hydrogen atom (hydrogen peroxide). For example and without being limitative, the hydroperoxide can be cumehe hydroperoxide (CHP), diisopropylbenzene dihydroperoxide or hydrogen peroxide, or a mixture thereof. Hydroperoxides are suitable for the detection of peroxidatic/pseudoperoxidatic activity.

In some implementations, the oxidizing agent may be a hydroperoxide precursor such as sodium percarbonate. Sodium percarbonate is a chemical adduct of sodium carbonate and hydrogen peroxide. The formula of sodium percarbonate is $2Na_2CO_3 \cdot 3H_2O_2$. Sodium percarbonate decomposes to sodium carbonate and hydrogen peroxide, for example upon contact with water.

In some implementations, the oxidizing agent is not initially added to the chromogenic absorbent material, but is generated in situ by a first catalytic compound present in the chromogenic absorbent material. It should be understood that "generated in situ" means that the oxidizing agent is directly synthesized in the chromogenic absorbent material from a precursor. For example, the first catalytic compound may be an enzyme such as an oxido-reductase. For example, the first catalytic compound may be glucose oxidase (GOx). Optionally, the precursor may be oxygen ($O_2$), which can be reduced to hydrogen peroxide in the presence of glucose oxidase. In an optional aspect, the reduction of the precursor to the oxidizing agent can take place in the presence of a saccharide or polysaccharide which can be oxidized by the first catalytic compound.

In some implementations, the oxidizing activity of the oxidizing agent is triggered by the presence of peroxidatic/pseudoperoxidatic activity in excretions. The oxidizing agent therefore oxidizes the chromogenic indicator which then changes of color. More particularly, the chromogenic indicator is an electron donor, i.e. a reducing agent that changes color upon losing an electron.

In some implementations, the chromogenic indicator is a benzidine-type compound, i.e. a compound as shown in formula I:

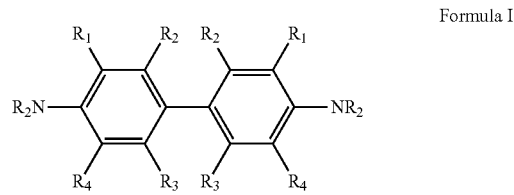

Formula I

In Formula I, groups $R_1$, $R_2$, $R_3$ and $R_4$ may be the same or different and may be hydrogen, halogen, a lower alkyl or alkoxy group containing 1 to 4 carbon atoms, a ($C_1$-$C_4$)-dialkylamino group, an acetylamino group, a nitro group or an aromatic group which may be substituted.

Optionally, the chromogenic indicator may be a compound as shown in Formula II:

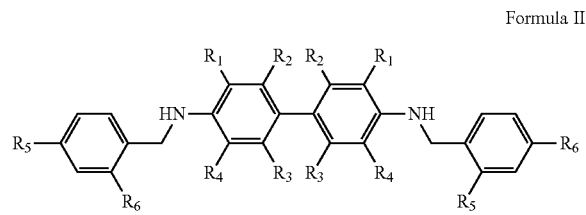

Formula II

In Formula II, groups $R_1$, $R_2$, $R_3$ and $R_4$ may be the same or different and represent hydrogen, halogen, and a lower alkyl or alkoxy group containing 1 to 4 carbon atoms, a ($C_1$-$C_4$)-dialkylamino group, an acetylamino group, a nitro group or an aromatic group which may be substituted; $R_5$ and $R_6$ are the same or different and represent water-soluble groups as hydroxyl group I, amino group, acidic group, disulfonyl group, ether group, halogen, and a lower alkyl or alkoxy group containing 1 to 4 carbon atoms, a ($C_1$-$C_4$)-dialkylamino group, an acetylamino group or a nitro group.

Thus, a water soluble benzidine-type chromogenic indicator of Formula II, responds in the presence of hydroperoxide and peroxidase by changing its light absorptive capability, which is due to the chemical transformation to the compound shown in Formula III:

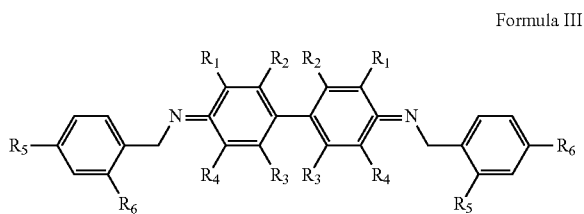

Formula III

It is understood that several different types of benzidine chromogenic indicators may be used.

Optionally, the chromogenic indicator may be 3,3',5,5'-tetramethylbenzidine (TMB). TMB is a colorless agent which turns blue upon oxidation. The peroxidase and/or pseudoperoxidase catalyze the oxidation of TMB by the oxidizing agent (hydroperoxide) according to the following oxidation reaction.

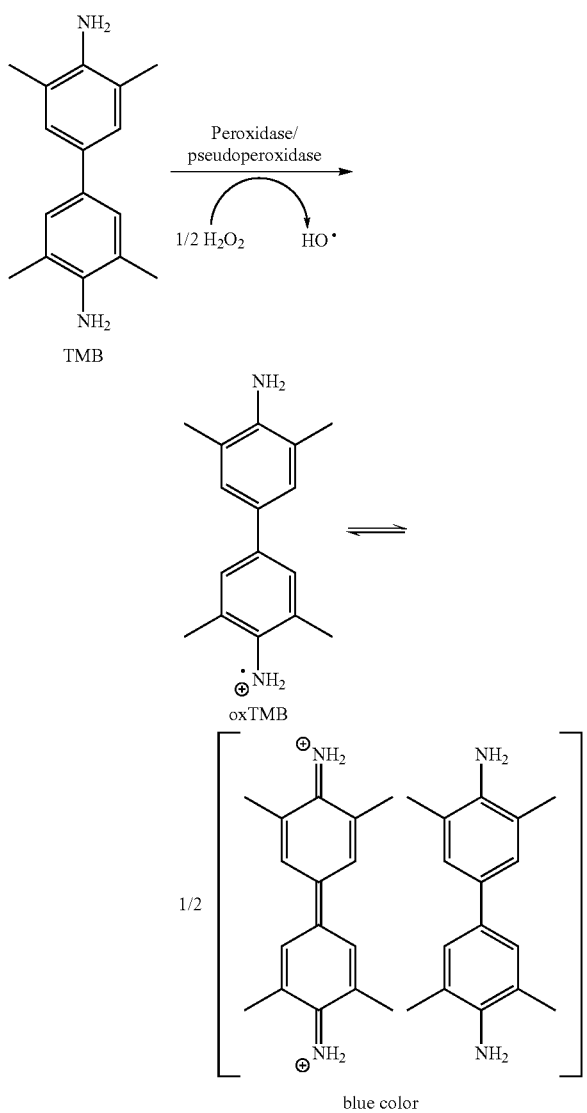

The absorptive material includes a water-absorbing polysaccharide providing absorptive properties to the chromogenic absorbent material. In some implementations, the water-absorbing polysaccharide may be a starch, a modified starch, amylopectin, amylose, modified amylose, a cellulose derivative, a gelling polysaccharide or a mixture thereof. Non-limiting examples of starches and modified starches are starch granules, pregelatinized starch, waxy starches, anionic starches, cationic starches, fractionated starches, cross-linked starches or mixtures thereof. Such starches may be obtained from many sources, including but not limited to wheat, maize, buckwheat, potato, cassava, sorghum, millet, oat, arrowroot, barley, beans, peas, rice, rye, and mixtures thereof. Non-limiting examples of cellulose derivatives are cellulose esters and cellulose ethers, or a mixture thereof. A non-limiting example of a cellulose ether is carboxymethyl cellulose (CMC). Non-limiting examples of gelling polysaccharides are agar-agar, guar and xanthan, or a mixture thereof.

Optionally, the water-absorbing polysaccharide can be a glass-like polysaccharide. Glass-like polysaccharides are substantially amorphous polysaccharides and include glass-like characteristics. Glass-like polysaccharides substantially lack an organized crystalline pattern. Glass-like polysaccharides are typically prepared by melting or heating the polysaccharide to a temperature above its glass-transition temperature, followed by cooling to a temperature below its glass transition or melting point temperature. A non-limiting example of a glass-like polysaccharide is pregelatinized starch.

Optionally, the absorptive material further includes a superabsorbent polymer (SAP). Optionally, the absorptive material includes in weight up to about 3 wt. %, or between 1 wt. % and 2.5 wt. % of the SAP. Non-limiting examples of SAP are poly(acrylic acids) and poly(methacrylic acids), salts thereof, or mixtures thereof. A non-limiting example of SAP is sodium polyacrylate, which is an efficient SAP. It should be understood that other types of SAPs may be used, such as superabsorbent starches or other synthetic superabsorbent polymers.

In an optional aspect, each particle of chromogenic absorbent material further includes a second polysaccharide providing structural integrity to the chromogenic absorbent material. By "providing structural integrity", it is meant that the second polysaccharide reduces or prevents the breaking up of the particles of chromogenic absorbent material upon handling or upon contact with an animal excretion. In other words, the second polysaccharide reduces the brittleness of the chromogenic absorbent material while preventing an increase of the softness or pliability of the chromogenic absorbent material. In some scenarios, the second polysaccharide provides sufficient structural integrity so that the particles of the chromogenic absorbent material cannot be easily broken or fractured by hand and are relatively unpliable and rigid solids.

For example, when the absorptive material consists of 100% pregelatinized starch, the particles of chromogenic absorbent material can tend to be soft and pliable and thus not as easily manipulated or deposited onto animal litter without being damaged. Upon contact with animal excretions, such pliable particles can still provide the desired color change and activity, but can be more easily crushed, torn or distorted by the animal.

Optionally, the second polysaccharide includes a crystalline polysaccharide. Examples of crystalline polysaccharides are cellulose, cellulose derivatives or mixtures thereof. In an optional aspect, the cellulose includes microcrystalline cellulose (MCC) or nanocrystalline cellulose (NCC), or a mixture thereof. In an optional aspect, the absorptive material includes in weight: about 35% to about 65%, or about 45% to 55% of the water-absorbing polysaccharide; and about 35% to about 65% or about 45% to about 55% of the second polysaccharide. In an optional aspect, the crystalline polysaccharide is less water-absorbent than the water-absorbing polysaccharide.

In some implementations, the chromogenic absorbent material may turn blue upon contact with excretions containing at least traces of blood (with therefore peroxidase/pseudoperoxidase activity).

It should be understood that "blue" refers to any shade of blue. The chromogenic absorbent material may need a contact time with excretions sufficient to enable coloration.

In an optional aspect, the particles may turn blue after a contact time ranging from about 10 seconds to about 30 min, or from about 10 seconds to about 1 min, depending on the nature of the absorptive material of the particles.

In some implementations, the chromogenic absorbent material may turn to different shades of blue depending on the blood or glucose concentration in excretions. The intensity of the blue shade may be proportional to the blood concentration or glucose concentration in excretions.

In some implementations, the chromogenic composition may further include a colour enhancer. Optionally, it may also include a buffering agent, a stabilizer, a metal scavenger agent or a combination thereof. The colour enhancer may optionally be 6-methoxyquinoline, lepidin, phenol derivatives, nitrobenzene, N-methylpyrrolidone, ethylene carbonate or any combination thereof. The buffering agent may optionally include citrate, sodium citrate, phosphate, acetate or any combination thereof. The stabilizer may optionally be ascorbic acid, ammonium molybdate and derivatives thereof, polyethylene glycol, polyvinylpyrrolidone, polyethylene oxide and derivatives thereof, or combination thereof. The metal-scavenger agent may optionally be EDTA, EDTA sodium salt or any combination thereof.

In some implementations, a chromogenic absorbent material is provided for detecting a detectable substance in an animal excretion. The chromogenic absorbent material includes:
- a trigger agent responsive to the presence of the detectable substance;
- a chromogenic indicator convertable into a chromogenically active substance in the presence of the trigger agent and the detectable substance; and
- an absorptive material for absorbing the animal excretion, the absorptive material being porous and including:
  - a water-absorbing polysaccharide providing absorptive properties to the chromogenic absorbent material; and
  - a second polysaccharide providing structural integrity to the chromogenic absorbent material.

It is understood that the trigger agent may be selected depending on the detectable substance and such that the conversion of the chromogenic indicator takes place and/or is catalyzed only if both the trigger agent and the detectable substance are present. For example, when the detectable substance is a peroxidase or a pseudoperoxidase, the trigger agent may be an oxidizing agent responsive to peroxidatic/pseudoperoxidatic activity in the animal excretion and the conversion of the chromogenic indicator includes oxidation into the chromogenically active substance.

In some implementations, the detectable substance includes a pseudoperoxidase (such as blood which includes haemoglobin), and the trigger agent is a hydroperoxide (such as cumene hydroperoxide) or a hydroperoxide precursor.

In some implementations, the detectable substance is glucose, and the trigger agent is a catalytic system including an oxido-reductase and a peroxidase, or an oxido-reductase and a pseudoperoxidase. For example, the oxido-reductase may be glucose oxidase and the peroxidase may be horseradish peroxidase.

In some implementations, depending on the absorptive material, the particles of chromogenic absorbent material may have a density of about 0.20 g/cm$^3$ to about 0.39 g/cm$^3$, of about 0.20 g/cm$^3$ to about 0.35 g/cm$^3$, of about 0.25 g/cm$^3$ to about 0.35 g/cm$^3$, or of about 0.30 g/cm$^3$ to about 0.35 g/cm$^3$.

In some implementations, depending on the absorptive material, the chromogenic absorbent material may have a total porosity of about 65% to about 85%, or of about 70% to about 80%. It is understood that the total porosity refers to the fraction of the bulk material volume (V) which is not occupied by solid matter. If the volume of solids is denoted by Vs, and the pore volume as Vpore=V−Vs, the total porosity can be expressed as shown in Equation 1 below.

$$\text{total porosity} = \phi = \frac{V - Vs}{V} = \frac{Vpore}{V} (\text{mL}/\text{mL}) \quad \text{Equation 1}$$

The total porosity may for example be measured by: placing a known volume of chromogenic absorbent particles into a container; covering the particles with a liquid; and measuring the volume of liquid needed to cover the particles (Vc). The total porosity is then expressed as the ratio of the volume of added liquid (Vc) to the volume of particles (V).

In some implementation, depending on the absorptive material, the particles of chromogenic absorbent material have an effective porosity of about 0.5 mL/g to about 2.0 mL/g, of about 0.6 mL/g to about 1.5 mL/g, of about 0.8 mL/g to about 1.2 mL/g or of about 0.9 mL/g to about 1.1 mL/g. It is understood that the effective porosity (also referred to as connected porosity or true porosity) is defined as the ratio of the connected pore volume to the total bulk volume. The effective porosity may for example be measured by: placing a known mass (m) of chromogenic absorbent particles into a container; covering the particles with a liquid; measuring the volume of liquid needed to cover the particles (Vc); removing the soaked particles from the container; measuring the liquid remaining in the container (Vr); and calculating the volume of liquid absorbed in the chromogenic absorbent particles (Va=Vc−Vr). The effective porosity may then be obtained as shown in Equation 2 below.

$$\text{effective porosity} = \phi_e = \frac{Vc - Vr}{m} = \frac{Va}{m} (\text{ml}/\text{g}) \quad \text{Equation 2}$$

It is to be noted that the effective porosity may also be expressed as the ratio Va/V in mL/mL.

In some implementations, the nature and form of the absorptive material may be selected and modified to allow sufficient internal diffusion and retention of excretions to facilitate the chromogenic indicator response over time. For example, the absorptive material may be modified so as to increase its porosity. The chromogenic indicator may also be homogeneously dispersed throughout the absorptive material according to the preparation method of the chromogenic absorbent material. The chromogenic indicator may be present not only at the exterior surface of a given particle, but also in a neighboring sub-surface region that can be rapidly exposed to excretions that are absorbed into the particle.

Additionally, when the absorptive material is glassy or substantially transparent, the presence of the chromogenic indicator in a sub-surface region allows it to be readily visible when a color change occurs and also avoids exposure to the air. In addition, the absorptive material may be provided with certain absorptive properties relative to the environment when in operation. For instance, the absorptive material may be provided to enable faster absorption of excretions compared to the surrounding material, such as surrounding animal litter, to facilitate adequate exposure of the excretions to the active agents in the chromogenic absorptive material. As different animal litters may have different absorptive properties, the absorptive material may be provided in accordance with pre-determined litter absorption properties, e.g. according to a maximum litter absorption rate. For instance, in some implementations, the absorptive material has a higher absorption rate compared to the litter material, and optionally a substantially higher absorption rate. For example, the absorptive material may have an absorption rate about 3 to 10 times higher, or about 5 to 10 times higher than the absorption rate of the litter material.

In some implementations, the chromogenic absorbent material has a free swelling capacity (FSC) greater than about 900%, or greater than about 1000%. The FSC is one type of measurement used for measuring the absorption properties of a material. An FSC measurement is performed by soaking the material to be tested in a liquid to be absorbed (in the present case, water) for a given time and weighing the material after the liquid has been absorbed. In some implementations, the chromogenic absorbent material has a higher FSC than compared to the litter material. For example, the chromogenic absorbent material may have a FSC about 1.5 to 2 times higher than the FSC of the litter material.

Figure 9:
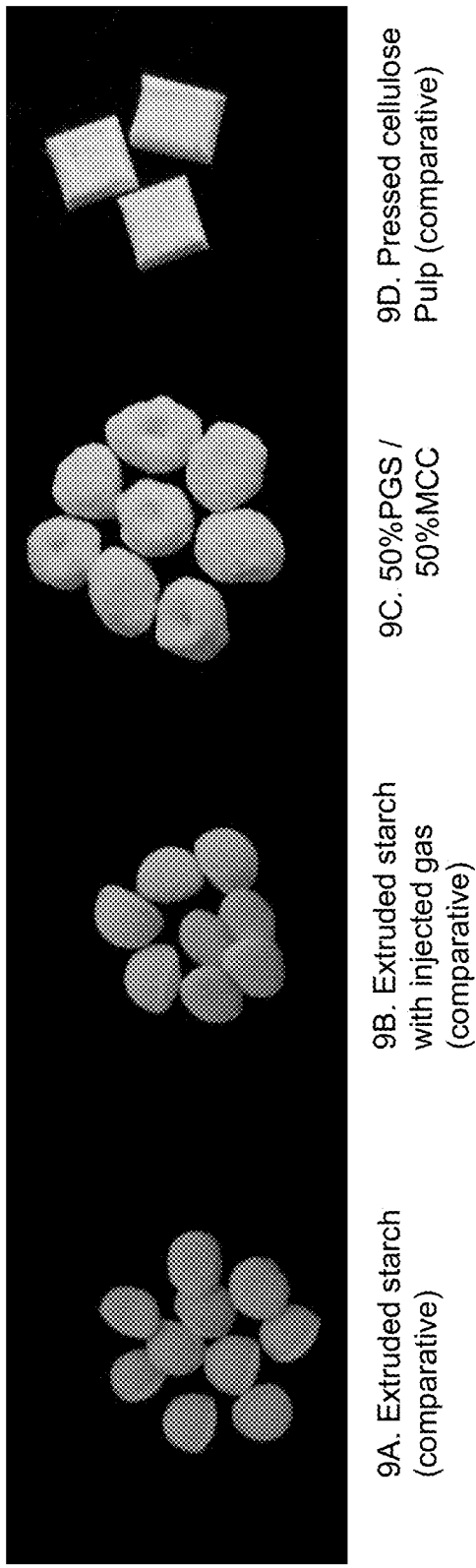
FIG. 9 shows photographs of extruded starch particles (9A, comparative), extruded starch particles in which gas was injected during extrusion (9B, comparative), particles of chromogenic absorbent material in which the absorptive material includes 50% PGS and 50% MCC (9C), and particles of pressed cellulose (9D, comparative).

Now referring to FIG. 9, a photograph showing different particles is shown. Particles 9A are extruded starch particles obtained under high shear, without injection of gas during extrusion. Particles 9A were made as a comparative example. Particles 9B are extruded starch particles obtained under high shear, with injection of gas during extrusion, Particles 9B were made as a comparative example. Particles 9D are pressed cellulose pulp particles and were also made as a comparative example. Particles 9C are chromogenic absorbent particles in which the absorptive material includes 50% pregelatinized starch (PGS) and 50% microcrystalline cellulose (MCC). Particles 9C were obtained through a process as described below and correspond to sample 25 as detailed in Example 2.

As can be seen in FIG. 9, particles 9A and 9B are in the form of compact pellets and particles 9D are in the form of pressed, compact squares. Particles 9C of chromogenic absorbent material are in the form of granules having a concave shape on one side and a convex shape on an opposite side. Of course, it is understood that the particles of chromogenic absorbent material may be of different shapes and be manufactured as pellets, granules, disks or squares, according to their process of manufacture.

Scanning electron micrographs of the particles of FIG. 9 were obtained in order to compare the morphology of particles 9A, 9B, 9C and 9D. Scanning electron micrographs showing the surface of the particles are shown in FIGS. 6A to 6D. Scanning electron micrographs showing cross sections of the particles are shown in FIGS. 7A to 7C and 8A to 8C. The scanning electron microscope used was a MEB JEOL JSM-5900LV™ (low vacuum).

Figure 6A:
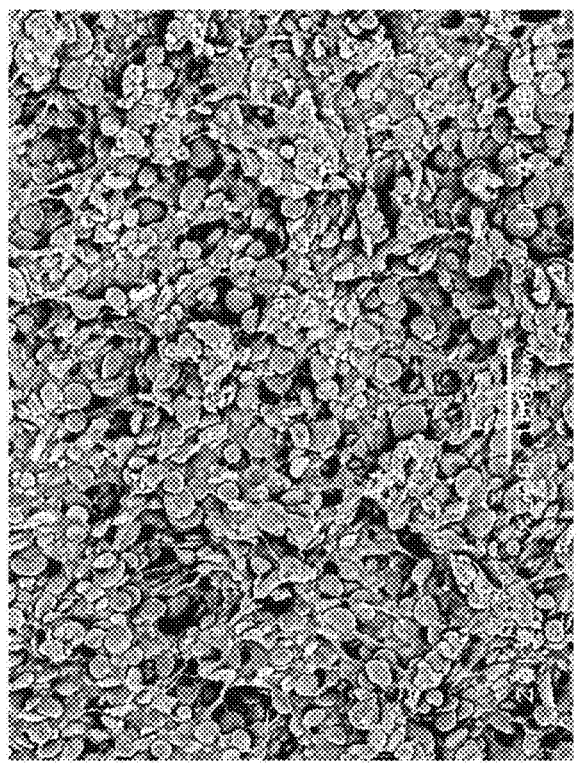
FIG. 6A is a ×200 scanning electron micrograph showing the surface of an extruded starch particle (comparative Figure).
Figure 6B:
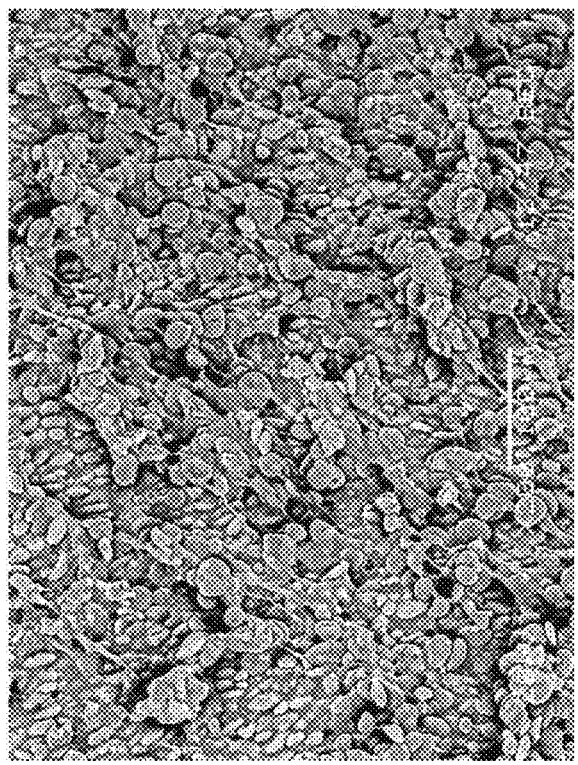
FIG. 6B is a ×200 scanning electron micrograph showing the surface of an extruded starch particle in which gas was injected during extrusion (comparative figure).

FIGS. 6A and 6B (comparative) show the surface of extruded starch particles obtained under high shear, with and without injected gas during extrusion. As can be seen, the surface of the extruded starch includes microscopic starch globules having a size of between about 5 μm and about 30 μm.

Figure 6D:
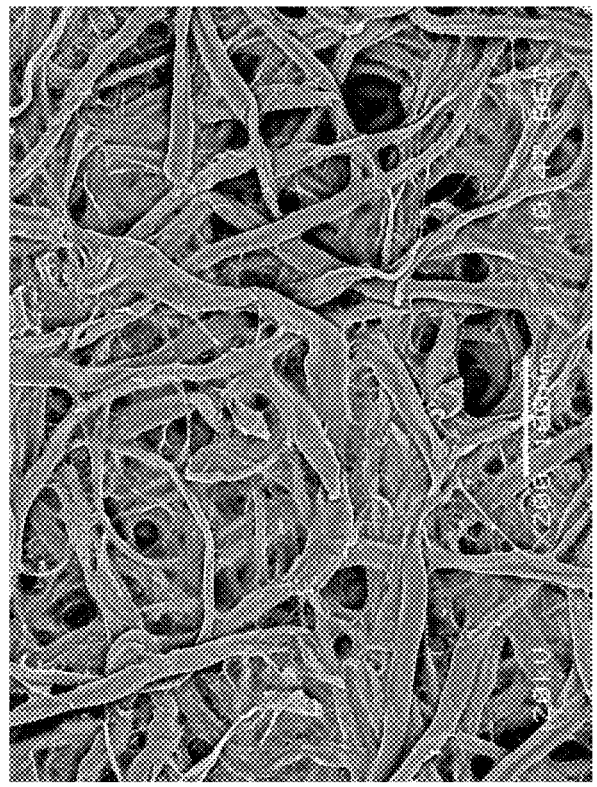
FIG. 6D is a ×200 scanning electron micrograph showing the surface of a particle of pressed cellulose (comparative figure).

FIG. 6D (comparative) shows the surface of pressed cellulose pulp particles. Elongated cellulose fibers can be seen on the surface. The fibers have a length of between about 100 μm and about 400 μm, and a width of between about 10 μm to about 30 μm.

Figure 6C:
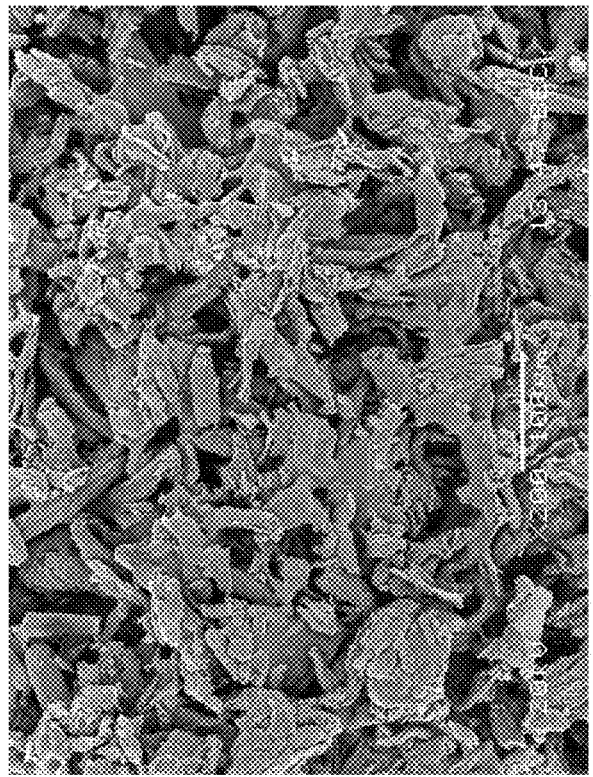
FIG. 6C is a ×200 scanning electron micrograph showing the surface of a particle of chromogenic absorbent material in which the absorptive material includes 50% PGS and 50% MCC.

FIG. 6C shows the surface of chromogenic absorbent particles in which the absorptive material includes 50% pregelatinized starch (PGS) and 50% microcrystalline cellulose (MCC). Microstructures of various shapes can be seen on the micrograph. The microsructures have a length of between about 10 μm to about 100 μm, and a width of between about 10 μm to about 100 μm.

Different microstructure morphologies are apparent for the different particles. The particles of FIGS. 6A and 6B mainly include a smooth globular microstructure, the particles of FIG. 6D mainly includes generally smooth filamentous microstructure, while the particles of FIG. 6C mainly include a rough, irregular, block-shaped microstructure.

The pore structure of the particles was also studied. Cross sections of the particles of chromogenic absorbent material were observed by scanning electron microscopy, as can be seen in FIG. 7C, and as detailed in Example 6. The cross sections were obtained by freeze-fracture under liquid nitrogen and observed by SEM to determine the pore density and equivalent diameter of the pores. It is understood that "pore density" refers to the proportion of the surface which is not covered by solid material (i.e., the ratio of the pore surface to the total surface). It is also understood that "equivalent diameter" refers to the approximate diameter of a comparable circular cylinder having the same volume as that of the pore.

Depending of the absorptive material, the particles of chromogenic absorbent material may have a pore density greater than about 20%, or greater than about 25%, or of about 27% to about 33%, for example. The pores of the particles of chromogenic absorbent material have an equivalent diameter greater than about 20 μm, or of about 20 μm to about 40 μm, or of about 20 μm to about 30 μm.

Figure 7B:
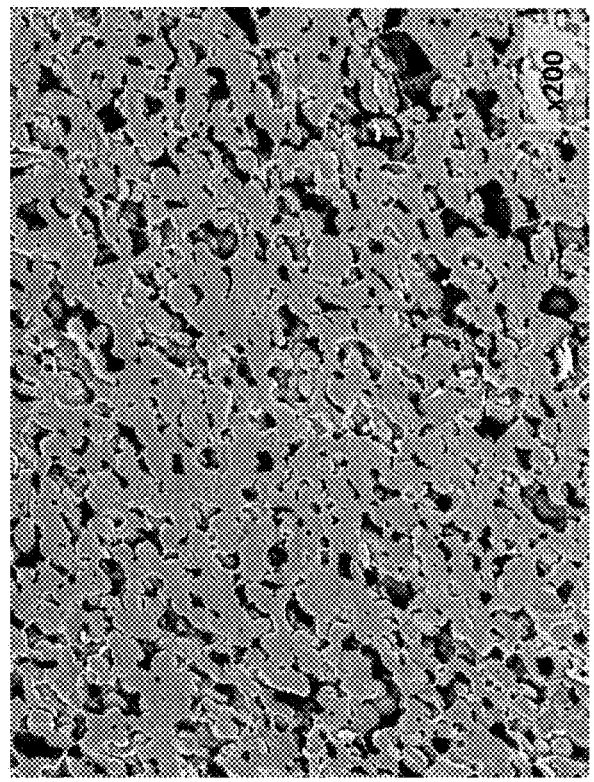
FIG. 7B is a ×200 scanning electron micrograph showing a cross section of an extruded starch particle in which gas was injected during extrusion. The cross section is obtained by freeze-fracture (comparative figure).
Figure 7A:
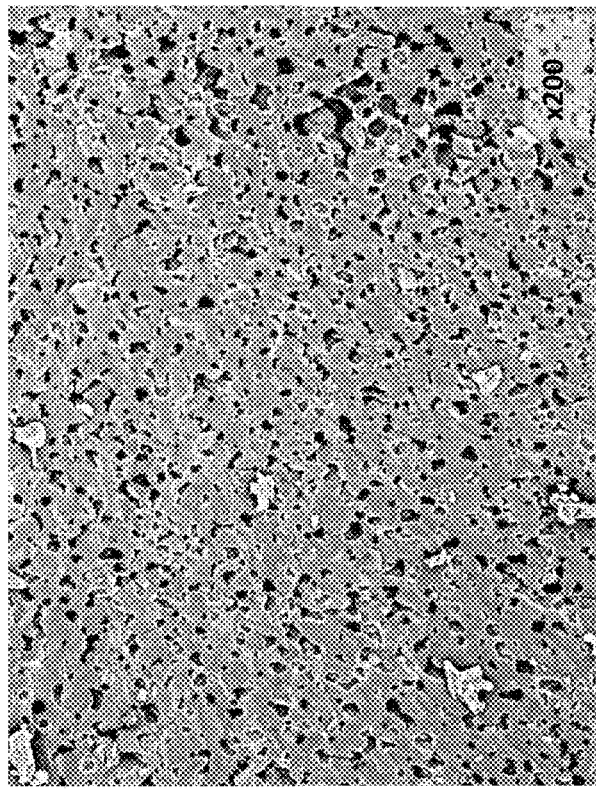
FIG. 7A is a ×200 scanning electron micrograph showing a cross section of an extruded starch particle, obtained by freeze-fracture (comparative Figure).
Figure 7C:
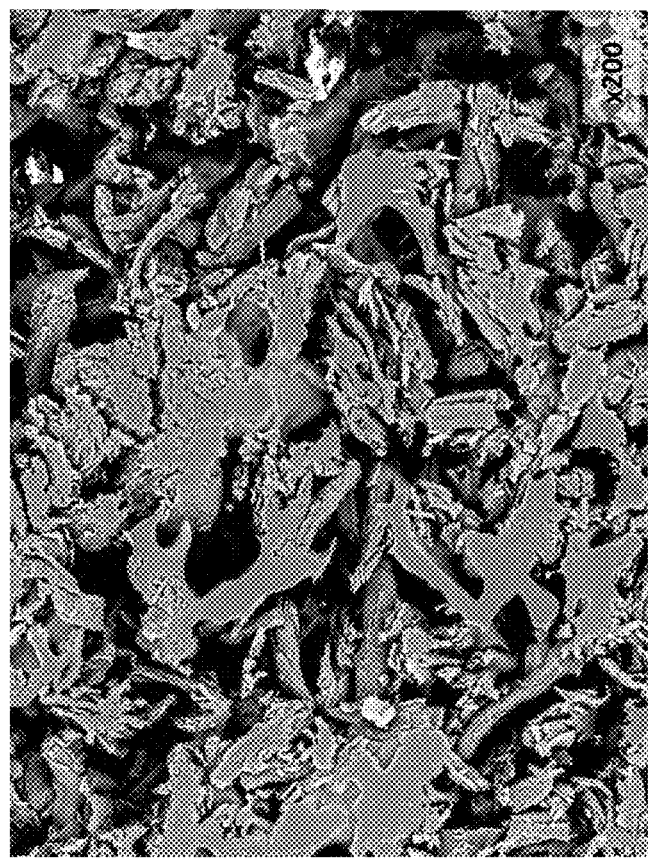
FIG. 7C is a ×200 scanning electron micrograph showing a cross section of a particle of chromogenic absorbent material in which the absorptive material includes 50% PGS and 50% MCC.
Figure 8B:
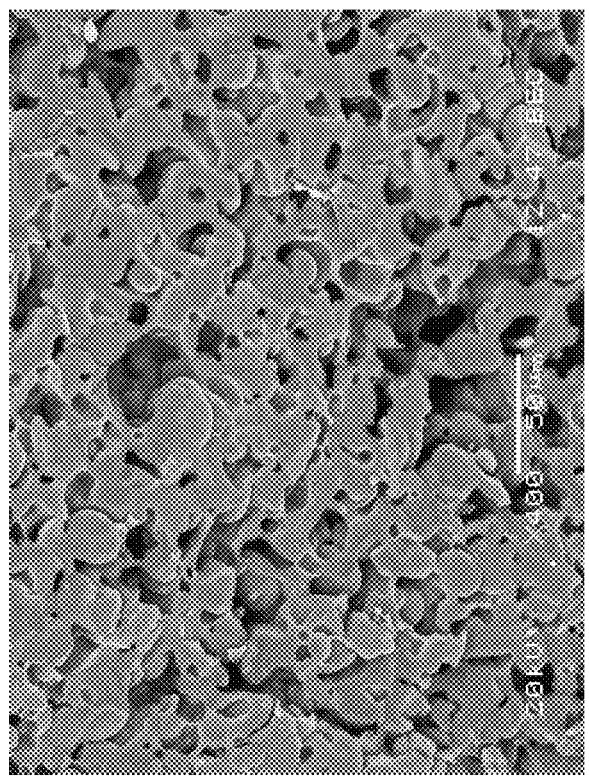
FIG. 8B is a ×400 scanning electron micrograph showing a cross section of an extruded starch particle in which gas was injected during extrusion. The cross section is obtained by freeze-fracture (comparative figure).
Figure 8A:
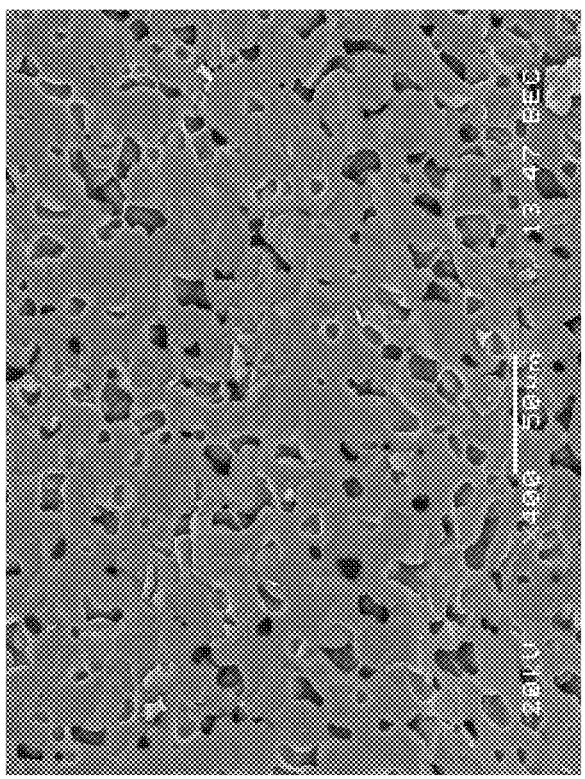
FIG. 8A is a ×400 scanning electron micrograph showing a cross section of an extruded starch particle, obtained by freeze-fracture (comparative Figure).
Figure 8C:
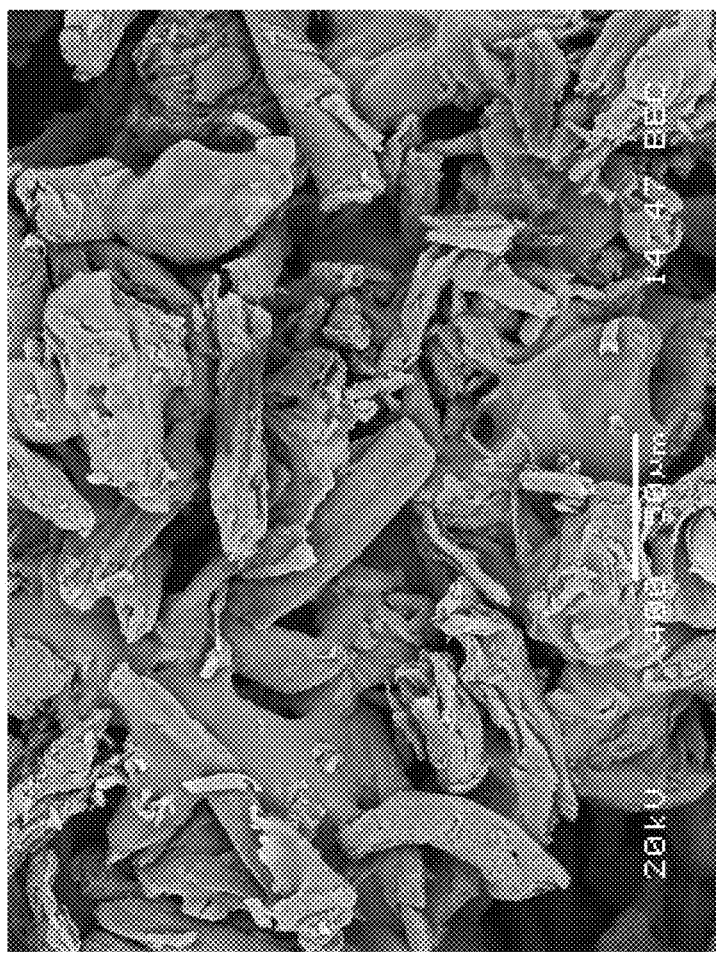
FIG. 8C is a ×400 scanning electron micrograph showing a cross section of a particle of chromogenic absorbent material in which the absorptive material includes 50% PGS and 50% MCC.

Cross sections of extruded starch particles were also examined as a comparative example (see also Example 6), and can be seen in FIGS. 7A and 7B.

Now referring to FIG. 1, an example of chromogenic absorbent material for detecting blood in animal excretions is described. The substance to be detected (blood) includes haemoglobin which is a pseudoperoxidase. In the absence of blood (i.e., in the absence of peroxidase and/or pseudoperoxidase), the reduction of cumene hydroperoxide (the oxidizing agent) into reduction products and the oxidation of TMB into oxidized TMB (oxTMB) is not catalyzed. When traces of blood are present (i.e., when traces of haemoglobin are present), the reactions are enabled and TMB is oxidized into oxTMB which has a distinctive blue color. The chromogenic absorbent material may be obtained to include a porous polysaccharide matrix having a low density. Thus, the chromogenic absorbent material described is suited for the detection of blood in animal excretions, and therefore for detection of urinary tract diseases for example.

Figure 2:
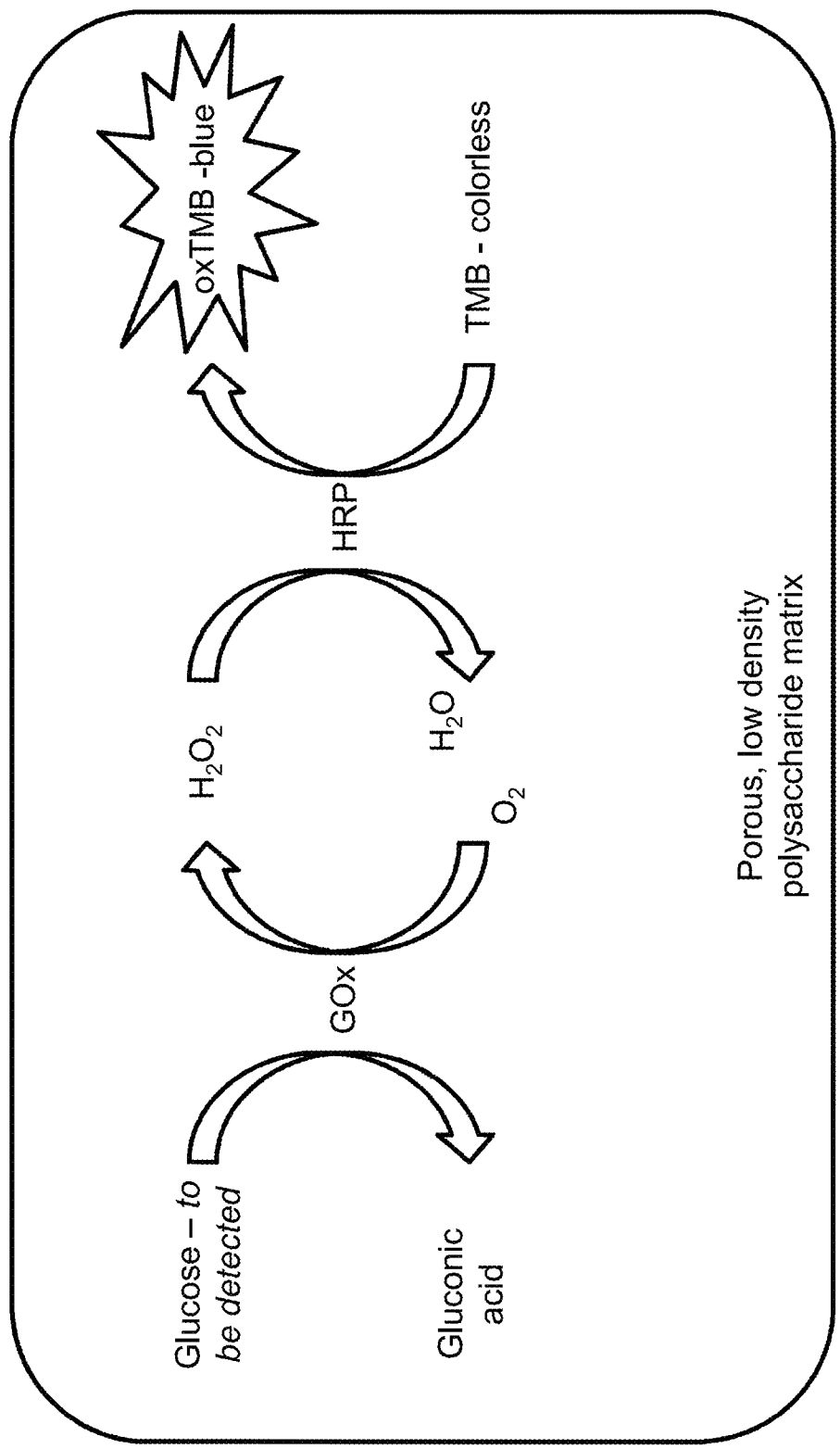
FIG. 2 is a scheme of the reaction pathway taking place in the particles of chromogenic absorbent material for the detection of glucose in animal excretions.

Now referring to FIG. 2, an example of the chromogenic absorbent material for detecting glucose in animal excretions is described. The chromogenic absorbent material used for detecting glucose includes a first catalytic compound (such as glucose oxidase) to generate hydrogen peroxide in situ. In the case of glucose detection, the chromogenic absorbent material further includes a second catalytic compound for catalyzing the oxidation of TMB and the reduction of the hydroperoxide. The second catalytic compound may be horseradish peroxidase. It is understood that other peroxidases or pseudoperoxidases may be used in other implementations. It should also be understood that in the case of glucose detection, the polysaccharide matrix does not include polysaccharides which may react with the first catalytic compound. If such polysaccharides were used, hydrogen peroxide would be generated in situ even without the presence of glucose in the animal excretions, which would lead to false positive test results. For example, when the first catalytic compound is glucose oxidase, the absorptive material does not include starches or modified starches that could react and give false positives.

Still referring to FIG. 2, when glucose is not present in the animal excretions, TMB is not oxidized, as no hydrogen peroxide is generated in situ. When glucose is present in the animal excretions, glucose oxidase oxidizes the glucose into gluconic acid and reduces oxygen into hydrogen peroxide. The horseradish peroxidase then reduces the hydrogen peroxide into water and oxidizes TMB into oxTMB which has a distinctive blue color. The chromogenic absorbent material described in FIG. 2 may be obtained to include a porous polysaccharide matrix having a low density, and is suited for detection of glucose in animal excretions, and therefore for detection of diabetes in animals for example.

In another aspect, a process of manufacturing particles of chromogenic absorbent material is provided. In some implementations, the process includes the steps of:
mixing together a water-absorbing polysaccharide, a second polysaccharide and optionally an superabsorbent polymer, thereby obtaining an absorptive powder mixture;
preparing a chromogenic solution by addition of a chromogenic agent and an oxidizing agent or by addition of the chromogenic agent and a first catalytic compound, into a solution;
combining the chromogenic solution with the absorptive powder mixture so as to obtain solution-impregnated humid particles; and
drying the solution-impregnated humid particles to obtain the chromogenic absorbent material.

It is understood that the step of mixing may not performed in scenarios where the absorptive powder only includes one polysaccharide.

The chromogenic solution includes either the chromogenic agent and the oxidizing agent or the chromogenic agent and a first catalytic compound for generating the oxidizing agent in situ. In the case of chromogenic solutions used for making particles of chromogenic absorbent material for the detection of glucose in animal excretions, the chromogenic solution further includes a second catalytic compound which may include a peroxidase, a pseudoperoxidase, or a mixture thereof.

Optionally, the chromogenic solution may include a buffering agent so as to maintain a pH of the chromogenic solution between 5 and 7. Extreme pH may be avoided.

Optionally, the chromogenic solution may include a colour enhancer, a stabilizer, a metal-scavenger agent or a combination thereof as defined above.

In an optional aspect, the chromogenic solution may be prepared and tailored to the particular absorptive material.

Optionally, the chromogenic solution may be combined with the absorptive material using a low-shear method. For example, the chromogenic solution may be combined with the absorptive material using a one-step granulation in a fluidized bed granulator. For example, the chromogenic solution may also be poured onto the absorptive powder mixture to obtain the solution-impregnated humid particles. In another example, the chromogenic solution may be poured onto the absorptive powder mixture to form the absorptive material, or dripped in the form of discrete drops onto the absorptive powder mixture such that the drops are impregnated with respective amounts of the powder to obtain corresponding discrete solution-impregnated humid particles.

Optionally, the solution-impregnated humid particles may be recovered by filtering the mixture of solution-impregnated humid particles and remaining absorptive powder through a sieve.

The drying step may be performed under vacuum and/or at various temperatures ranging from ambient temperature to about 65° C.

Using low-shear methods as described above allows for the manufacture of particles of chromogenic absorbent material having a lower density, a higher porosity, different morphology, and enhanced absorption properties compared with other types of particles obtained by methods such as extrusion or pressing.

EXAMPLES

Example 1

Experiments were performed by preparing particles of chromogenic absorbent material having different compositions and testing the particles when contacted with a blood-containing solution.

Particles of chromogenic absorbent material were prepared by mixing pregelatinized starch (PGS), microcrystalline cellulose (MCC) and sodium polyacrylate as the superabsorbent polymer (SAP), in powder form, thereby obtaining an absorptive powder mixture; pouring the chromogenic solution on the absorptive powder mixture to obtain solution-impregnated humid particles; and drying the solution-impregnated humid particles in an oven at 65° C. to obtain the particles of chromogenic absorbent material. In this case, the particles of chromogenic absorbent material are in the form of granules having a length of between about 0.25 cm and about 0.75 cm.

The chromogenic solution I that was used is detailed in Table 1:

TABLE 1

| Compound | Molar mass (g/mol) | Mass or volume | Concentration (mmol/L) |
|---|---|---|---|
| Water (solvent) | — | 50 mL | — |
| Acetone (solvent) | — | 50 mL | — |
| TMB (chromogenic indicator) | 240.34 | 312 mg | 13 |
| CHP (oxidizing agent) | 152.19 | 114 mg | 7.5 |
| 4-lepidine (color enhancer) | 143.19 | 107 mg | 7.5 |
| Polyvinylpyrrolidone (stabilizer) | — | 30 mg | — |
| Ascorbic acid (stabilizer) | 176.12 | 20 mg | 1.15 |

The particles of chromogenic absorbent material were prepared with varying ratios of PGS/MCC and a varying amount of sodium polyacrylate-based SAP, and are numbered as shown in Table 2:

TABLE 2

|  | 0 wt. % sodium polyacrylate | 1 wt. % sodium polyacrylate | 2 wt. % sodium polyacrylate | 3 wt. % sodium polyacrylate |
|---|---|---|---|---|
| 35% PGS/ 65% MCC | 1 | 2 | 3 | 4 |
| 40% PGS/ 60% MCC | 5 | 6 | 7 | 8 |
| 45% PGS/ 55% MCC | 9 | 10 | 11 | 12 |
| 55% PGS/ 45% MCC | 13 | 14 | 15 | 16 |
| 60% PGS/ 40% MCC | 17 | 18 | 19 | 20 |
| 65% PGS/ 35% MCC | 21 | 22 | 23 | 24 |

The particles of chromogenic absorbent material shown in Table 2 were placed on a bentonite-based litter and contacted with 5 mL of a 0.0215% blood solution or 5 mL of demineralized water which did not contain blood. Particles which were not contacted with any solution were also placed on the litter as a negative control.

FIGS. 3A, 3B, 3C and 3D illustrate samples as numbered in Table 2, and placed on a bentonite-based litter. In each figure, the top picture shows the granules 30 minutes after contact with the solutions, the middle picture shows the granules 2 hours after contact, and the bottom picture shown the granules 18 hours after contact. In each picture of each Figure, the top row of granules is the negative control; the middle row shows granules contacted with 5 mL of demineralized water which did not contain blood; and the bottom row shows granules contacted with 5 mL of a 0.0215% blood solution.

Figure 3A:
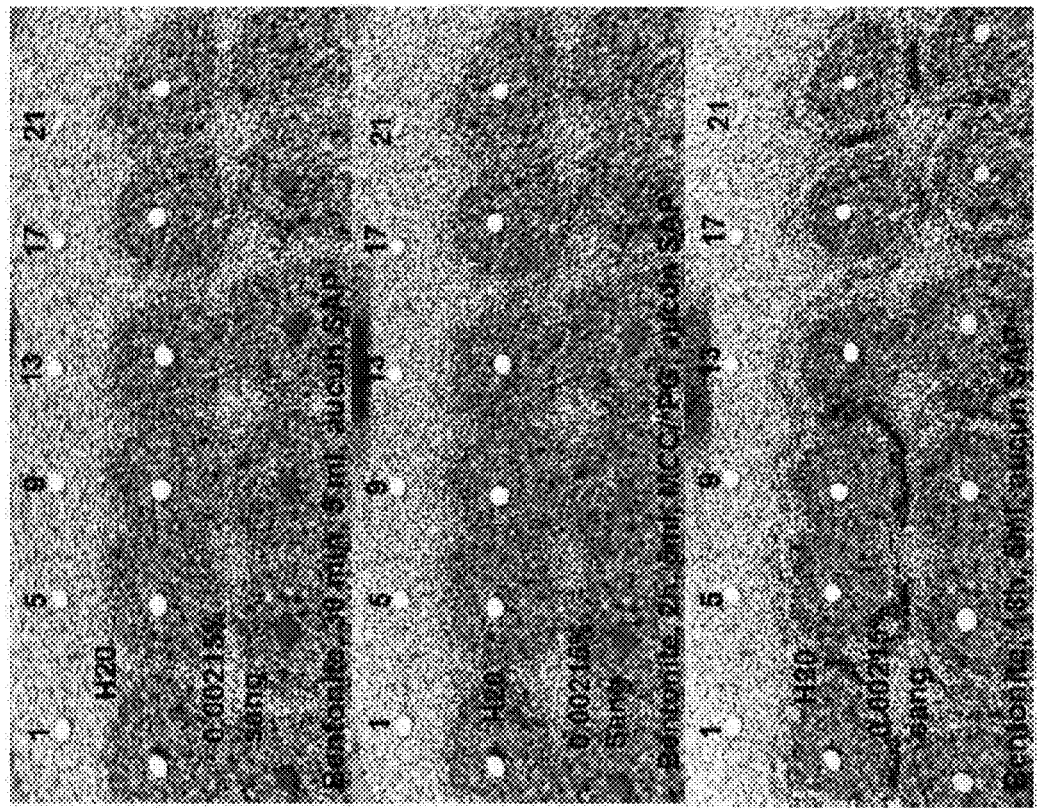
FIG. 3A shows photographs of six samples of particles of chromogenic absorbent materials after 30 minutes, 2 hours and 18 hours of contact with a diluted blood solution.
Figure 3B:
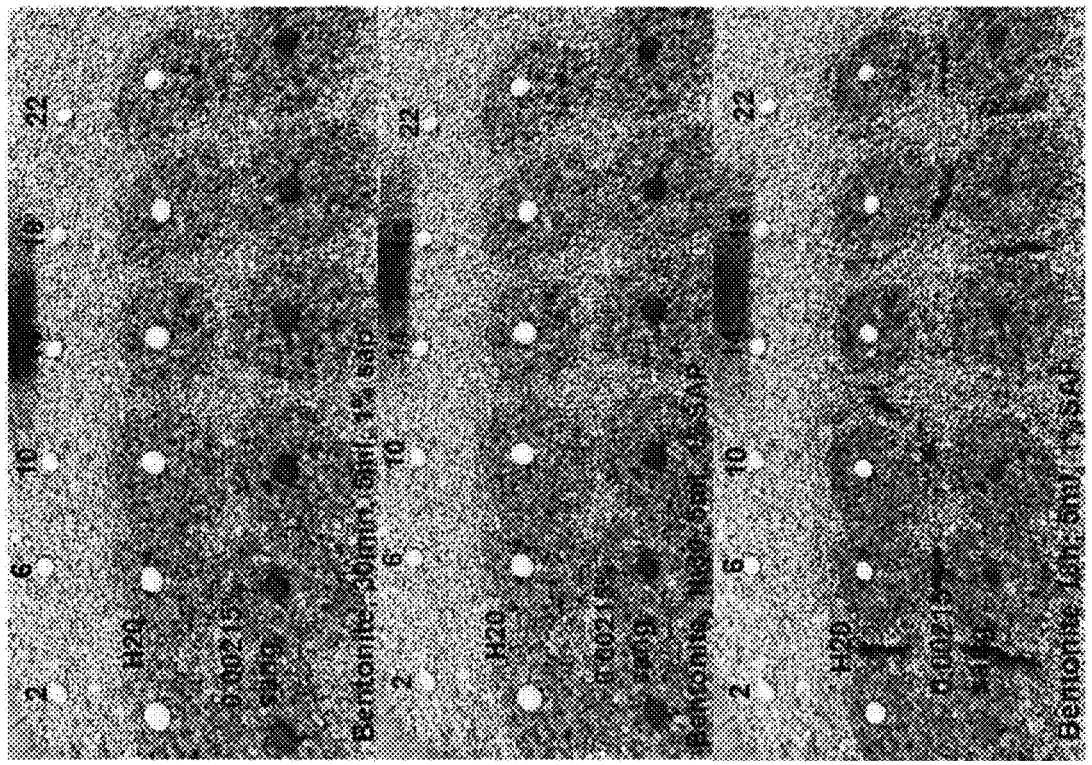
FIG. 3B shows photographs of six samples of particles of chromogenic absorbent materials including 1% of superabsorbent polymer after 30 minutes, 2 hours and 18 hours of contact with a diluted blood solution.

As can be seen in FIG. 3A, granules No. 1, 5, 9, 13, 17 and 21 were contacted with the different solutions (these granules contained 0 wt. % of superabsorbent polymer). The granules contacted with demineralized water did not change color and had the same white color as the negative control granules 30 mins, 2 h and 18 h after contact. The granules contacted with the blood solution had already turned blue 30 mins after contact. The blue coloration was distinctive. 2 h after contact, the blue coloration was still distinctive and present. 18 h after contact, the blue coloration had faded and the granules turned off-white or yellow. The blue coloration was present and distinctive for about 8 hours before fading. As can be seen in FIG. 3B, granules No. 2, 6, 10, 14, 18 and 22 were contacted with the different solutions (these granules contained about 1 wt. % of superabsorbent polymer). The granules contacted with demineralized water did not change color and had the same white color as the negative control granules 30 mins, 2 h and 18 h after contact. The granules contacted with the blood solution had already turned blue 30 mins after contact. The blue coloration was distinctive. 2 h after contact, the blue coloration was still distinctive and present. 18 h after contact, the blue coloration was still distinctive and present. The addition of 1 wt. % SAP had a positive effect on the retention of blue coloration in the granules after contact with a blood solution.

Figure 3C:
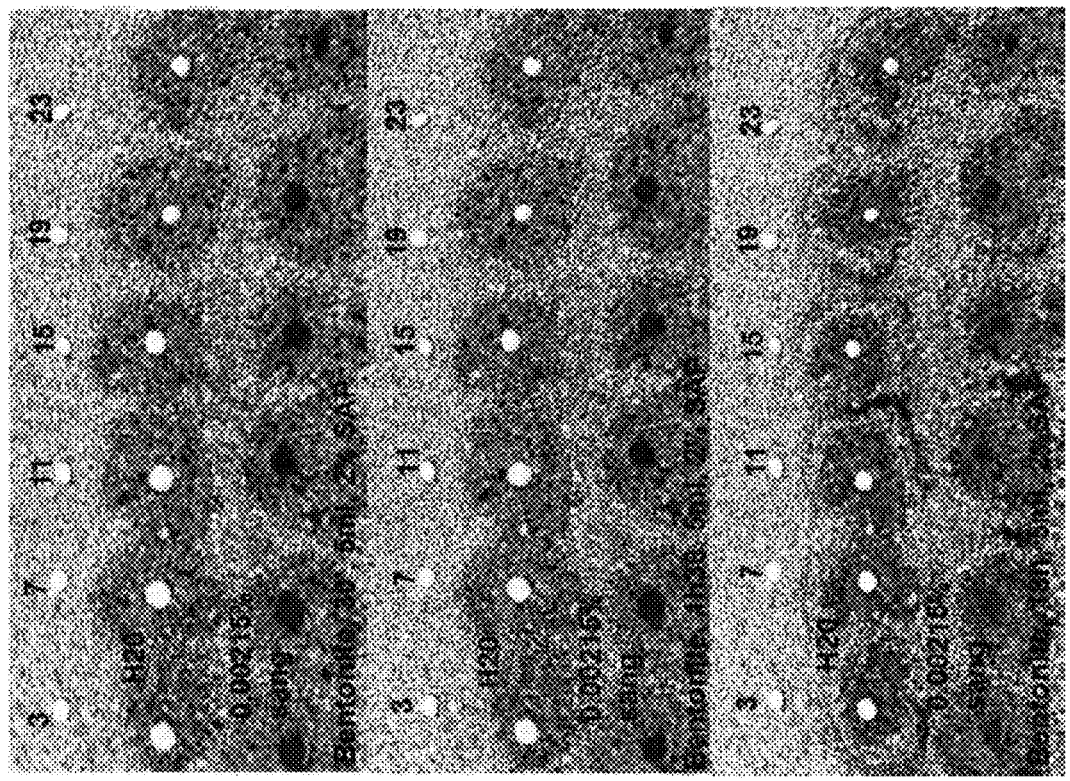
FIG. 3C shows photographs of six samples of particles of chromogenic absorbent materials including 2% of superabsorbent polymer after 30 minutes, 2 hours and 18 hours of contact with a diluted blood solution.

As can be seen in FIG. 3C, granules No. 3, 7, 11, 15, 19 and 24 were contacted with the different solutions (these granules contained about 2 wt. % of superabsorbent polymer). The same results as the ones observed and illustrated in FIG. 3B were obtained.

Figure 3D:
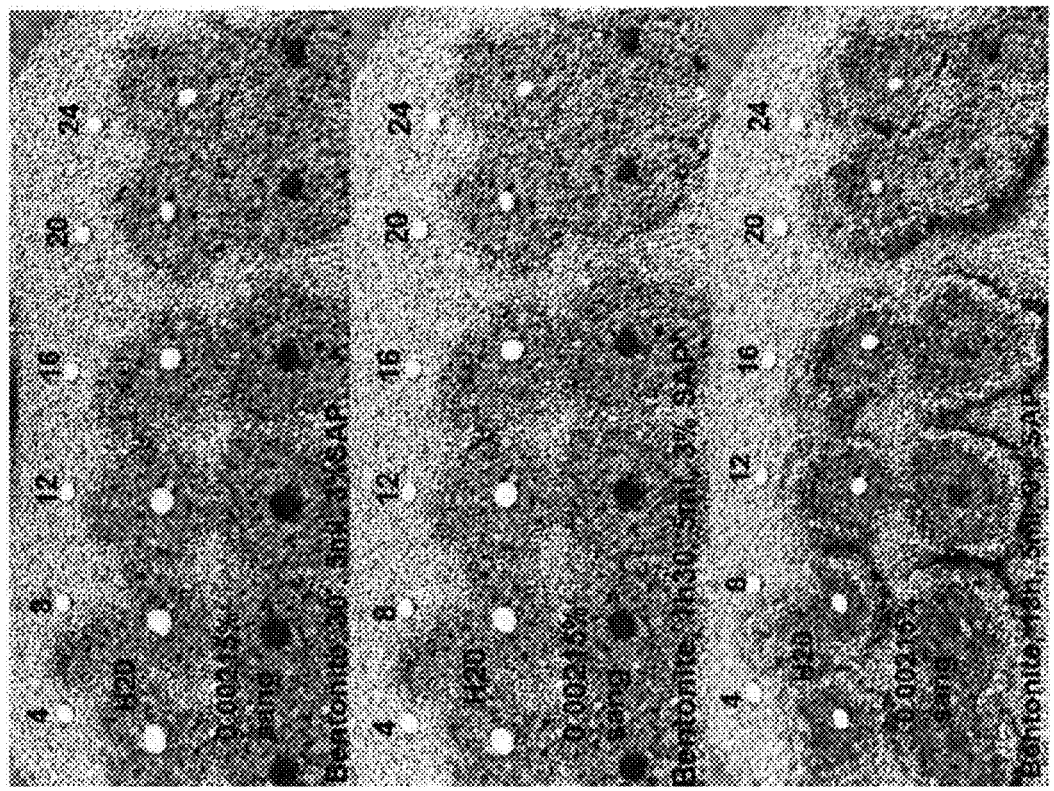
FIG. 3D shows photographs of six samples of particles of chromogenic absorbent materials including 3% of superabsorbent polymer after 30 minutes, 2 hours and 18 hours of contact with a diluted blood solution.

As can be seen in FIG. 3D, granules No. 4, 8, 12, 16, 20 and 25 were contacted with the different solutions (these granules contained about 3 wt. % of superabsorbent polymer). The same results as the ones observed and illustrated in FIGS. 3B and 3C were obtained.

Example 2

Experiments were performed by preparing particles of chromogenic absorbent material using different polysaccharides and mixtures thereof, and testing said particles when contacted with a blood-containing solution. The polysaccharides used in this Example were pregelatinized starch (PGS), microcrystalline cellulose (MCC) and carboxymethylcellulose (CMC).

The particles were prepared as described in Example 1. No superabsorbent polymer was used in this Example and the mixing step was not performed when only one polysaccharide was used. The same chromogenic solution I as described in Example 1 was also used.

Particles of chromogenic absorbent material were prepared using various polysaccharides and mixtures thereof, and are numbered as shown in Table 3.

TABLE 3

| Polysaccharide or polysaccharide mixture | Sample number |
|---|---|
| 50% PGS/50% MCC | 25 |
| 100% CMC | 26 |
| 100% PGS | 27 |

Figure 4:
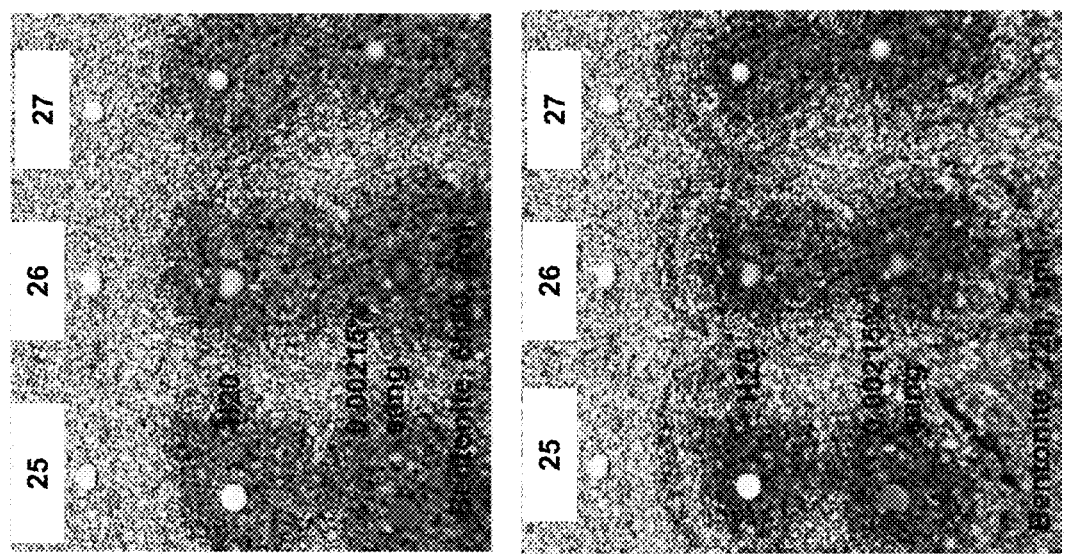
FIG. 4 shows photographs of three samples of particles of chromogenic absorbent materials including after 6 h 30 and 22 hours of contact with a diluted blood solution.

FIG. 4 shows the granules 6 h 30 and 22 h after contact with 5 mL of demineralized water which did not contain blood (middle row) or 5 mL of a 0.0215% blood solution (bottom row). The top row is the negative control showing granules which were not contacted with either solution. A deep blue coloration rapidly appeared a few minutes after contact with the blood-containing solution (not shown). The granules contacted with demineralized water stayed substantially white or became slightly yellow. After 6 h 30, samples No. 25 and 26 retained the deep blue coloration, while the blue coloration of sample No. 27 was lighter. After 22 h, sample No. 25 retained the deep blue coloration, sample No. 26 had a light blue coloration, and the coloration of sample No. 27 had substantially faded.

It is to be noted that all the samples prepared enable the detection of blood. Using 50% PGS/50% MCC as the absorptive material enabled the blue coloration to be retained for a longer period when compared with 100% CMC and 100% PGS granules.

Example 3

Experiments have been performed by preparing particles of chromogenic absorbent material using a mixture of 50% microcrystalline cellulose (MCC) and 50% carboxymethyl cellulose (CMC) as the absorptive material, and different chromogenic solutions. Said particles were contacted with glucose-containing solutions.

The composition of the chromogenic solution II is detailed in Table 4.

TABLE 4

| Solvents and compounds | Mass or volume |
|---|---|
| Water (solvent) | 50 mL |
| Acetone (solvent) | 50 mL |
| TMB (chromogenic indicator) | 312 mg |

TABLE 4-continued

| Solvents and compounds | Mass or volume |
| --- | --- |
| Glucose oxidase (first catalytic compound) | 6 mg |
| Horseradish peroxidase (second catalytic compound) | 5 mg |

Chromogenic solution II shown in Table 4 was diluted at ratios of 1:2 and 1:10 to obtain chromogenic solutions III (1:2 dilution) and IV (1:10 dilution).

Particles of chromogenic absorbent material were prepared by mixing carboxymethyl cellulose (CMC) and microcrystalline cellulose (MCC), thereby obtaining an absorptive powder mixture; pouring chromogenic solution II, III or IV on the absorptive powder mixture to obtain solution-impregnated humid particles; and drying the solution-impregnated humid particles in an oven at 65° C. to obtain the particles of chromogenic absorbent material. In this case, the particles of chromogenic absorbent material were obtained in the form of granules.

Figure 5:
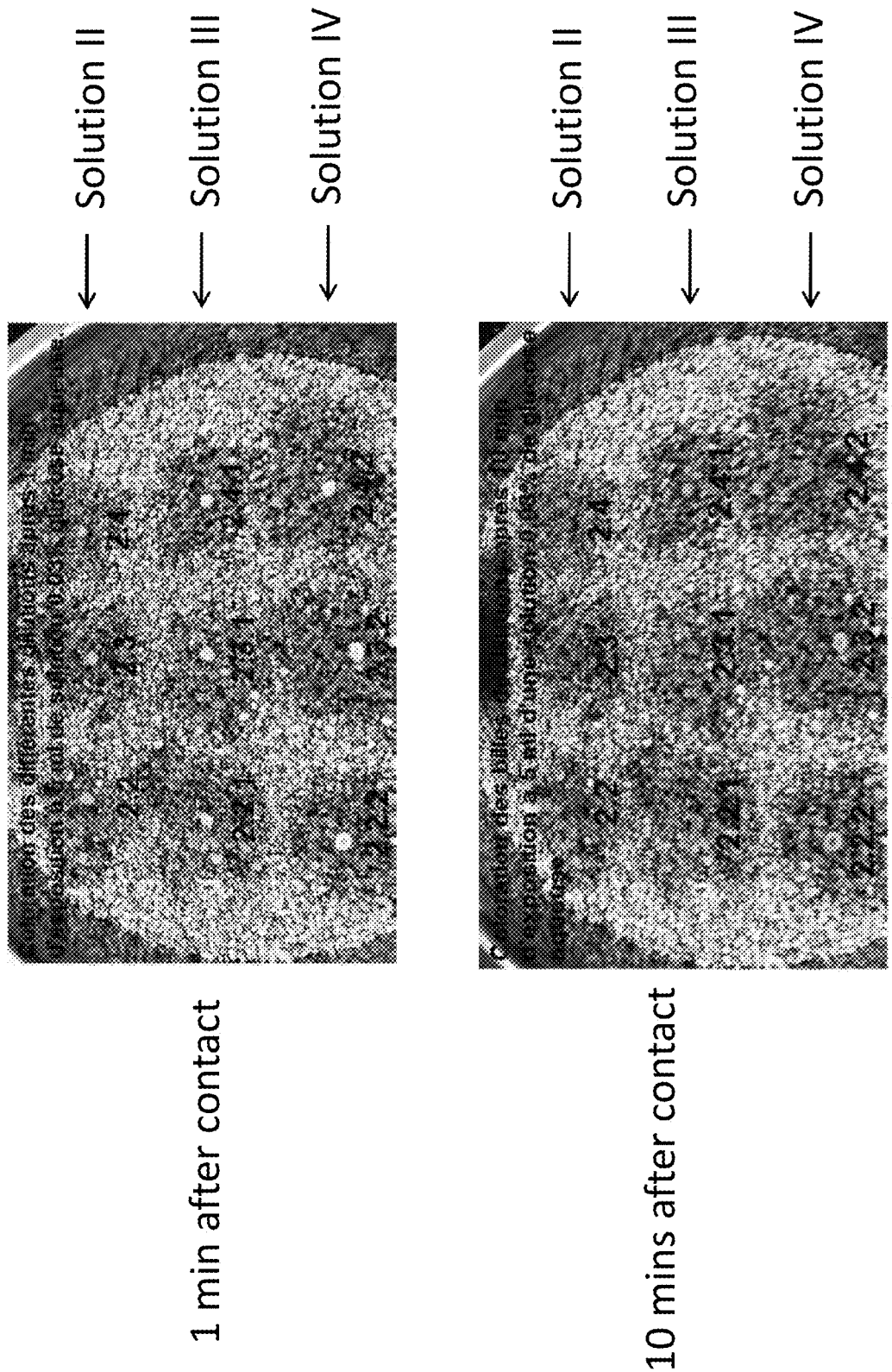
FIG. 5 shows photographs of samples of particles of chromogenic absorbent materials including after 1 minute and 10 minutes of contact with glucose solutions of different concentrations.

FIG. 5 shows particles of chromogenic absorbent material 1 minute (top picture) and 10 minutes (bottom picture) after contact with a solution containing 0.03% of glucose. In each picture, the top row corresponds to chromogenic absorbent material made with chromogenic solution II, the middle row corresponds to chromogenic absorbent material made with chromogenic solution III, and the bottom row corresponds to chromogenic absorbent material made with chromogenic solution IV. As can be seen, when the more concentrated solution II was used, the blue coloration is deeper and appears within 1 minute of contact. When the lower concentration solution IV is used, the deep blue coloration appeared within 10 minutes of contact.

Example 4

Experiments were also performed by measuring the free swelling capacity (FSC) of particles of chromogenic absorbent material. The particles of chromogenic absorbent material were prepared as described in Example 1 using PGS, Xanthan or guar as the water-absorbing polysaccharide, and MCC. The measurements were performed by soaking the samples in water for 30 minutes and draining the water remaining at the surface for 10 minutes. The values obtained were compared with the FSC values of particles obtained by extrusion or pressing. The results are detailed in Table 5.

TABLE 5

| Particle type | FSC % |
| --- | --- |
| Extruded starch granule without gas injection (comparative) | 190 |
| Extruded starch granule with gas injection (comparative) | 200 |
| Pressed paper pulp pellet (comparative) | 500 |
| 50% PGS/50% MCC granule (sample No. 25 of Example 2) | 1080 |
| 50% Xanthan/50% MCC granule | 3360 |
| 50% guar gum/50% MCC granule | 2030 |

The particles of chromogenic absorbent material made from PGS/MCC, xanthan/MCC and guar gum/MCC all exhibit high FSC values. This is indicative of a very high porosity and surprisingly high absorption properties when compared with the extruded starch granules and pressed paper pulp pellets known in the art.

Example 5

Experiments have also been performed by measuring the density of particles of chromogenic absorbent material. The particles of chromogenic absorbent material were prepared as described in Example 1 using PGS, Xanthan or guar as the water-absorbing polysaccharide, and MCC. The values obtained were compared with the density values of particles known in the art and obtained by extrusion or pressing. The results are detailed in Table 6.

TABLE 6

| Particle type | Density (g/cm$^3$) |
| --- | --- |
| Extruded starch granule without gas injection (comparative) | 0.60 |
| Extruded starch granule with gas injection (comparative) | 0.48 |
| Pressed paper pulp pellet (comparative) | 0.40 |
| 50% PGS/50% MCC granule (sample No. 25 of Example 2) | 0.33 |
| 50% Xanthan/50% MCC granule | 0.37 |
| 50% guar gum/50% MCC granule | 0.26 |

The particles of chromogenic absorbent material made from PGS/MCC, xanthan/MCC and guar gum/MCC exhibit lower density values when compared with the extruded starch granules and pressed paper pulp pellets known in the art.

Example 6

Experiments have been performed to obtain scanning electron micrographs of cross sections of particles of extruded starch with or without injected gas during extrusion (FIGS. 7A and 7B, comparative) and of a cross section of a particle of chromogenic absorbent material corresponding to sample 25 as shown in Example 2 (FIG. 7C). The images obtained were analyzed to determine the pore density and the equivalent diameter of the pores. Prior to imaging, the respective particles were first hardened by freezing in liquid nitrogen and cut in the frozen state. The scanning electron microscope used was a MEB JEOL JSM-5900LV™ (low vacuum).

The pore density and equivalent diameter measurements were performed by using the Nikon NIS-Elements D™ image analysis software. The results are detailed in Table 7.

TABLE 7

| Particle type | Pore density (%) | Equivalent diameter (μm) |
| --- | --- | --- |
| Extruded starch granule without gas injection (comparative) | 7.6 | 7.8 |
| Extruded starch granule with gas injection (comparative) | 10.8 | 11.5 |
| 50% PGS/50% MCC granule (sample No. 25 of Example 2) | 29.5 | 25.3 |

The particles of corresponding to sample No. 25 of Example 2 have a higher pore density and equivalent pore diameter than the particles of extruded starch (made with or without gas injection during high shear extrusion).

Example 7

Experiments have been performed on sample No. 25 of Example 2 to measure the total porosity and effective porosity of particles of chromogenic absorbent material. Comparative measurements were also performed on extruded starch granules (with or without injected gas during high shear extrusion). The porosity measurements were performed as follows.

200 mL of particles were placed in a container. The particles were weighed (mass m). Acetone was added to soak the particles and completely cover the particles with solvent. The volume of solvent required to cover all the particles was measured (Vc). The soaked particles were removed from the container and the volume of remaining solvent was measured (Vr). The volume of liquid absorbed by the chromogenic absorbent particles (Va=Vc−Vr) was calculated. The total porosity is then obtained by calculating the ratio of the volume of added liquid (Vc) to the volume of particles (V), and the effective porosity is calculated using Equation 2 detailed above. The results are summarized in Table 8.

TABLE 8

| Particle type | Mass of particles (g) | Vc (mL) | Va (mL) | Total porosity (%) | Effective porosity (mL/g) |
|---|---|---|---|---|---|
| Extruded starch granule without gas injection (comparative) | 120 | 104 | 18 | 52% | 0.15 |
| Extruded starch granule with gas injection (comparative) | 96 | 116 | 16 | 58% | 0.167 |
| 50% PGS/50% MCC granule (sample No. 25 of Example 2) | 66 | 150 | 65 | 75% | 0.985 |

As can be seen, the particles of chromogenic absorbent material made of 50% PGS and 50% MCC have an effective porosity which is substantially higher than extruded starch particles obtained with or without gas injection during high shear extrusion.

The invention claimed is:

1. A chromogenic absorbent material for detecting a detectable substance in an animal excretion, the chromogenic absorbent material comprising:
a trigger agent;
a chromogenic indicator oxidizable into a colored and/or fluorescent substance in the presence of the trigger agent and the detectable substance; and
an absorptive material which is porous, for absorbing the animal excretion, the absorptive material comprising a water-absorbing polysaccharide;
wherein the chromogenic absorbent material has a density of about 0.20 g/cm3 to about 0.39 g/cm3.

2. The chromogenic absorbent material of claim 1, wherein:
the detectable substance is a peroxidase or a pseudoperoxidase; and
the trigger agent is an oxidizing agent responsive to peroxidatic/pseudoperoxidatic activity in the animal excretion.

3. The chromogenic absorbent material of claim 2, wherein the pseudoperoxidase is hemoglobin.

4. The chromogenic absorbent material of claim 2, wherein the trigger agent is a hydroperoxide or a hydroperoxide precursor.

5. The chromogenic absorbent material of claim 1, wherein:
the detectable substance is glucose; and
the trigger agent is a catalytic system comprising a first enzyme which is an oxido-reductase and a second enzyme which is a peroxidase or a pseudoperoxidase.

6. The chromogenic absorbent material of claim 5, wherein the first enzyme is glucose oxidase and the second enzyme is horseradish peroxidase.

7. The chromogenic absorbent material of claim 1, wherein the water-absorbing polysaccharide comprises a starch, a modified starch, a cellulose derivative or a gelling polysaccharide, or a mixture thereof.

8. The chromogenic absorbent material of claim 1, wherein the water-absorbing polysaccharide comprises pregelatinized starch.

9. The chromogenic absorbent material of claim 1, wherein the absorptive material further comprises a second polysaccharide providing structural integrity to the chromogenic absorbent material.

10. The chromogenic absorbent material of claim 9, wherein the second polysaccharide comprises a crystalline polysaccharide.

11. The chromogenic absorbent material of claim 10, wherein the crystalline polysaccharide comprises cellulose, a cellulose derivative or mixtures thereof.

12. The chromogenic absorbent material of claim 11, wherein the cellulose comprises microcrystalline cellulose (MCC), nanocrystalline cellulose (NCC), or a mixture thereof.

13. The chromogenic absorbent material of claim 9, wherein the absorptive material comprises:
about 35 wt. % to about 65 wt. % of the water-absorbing polysaccharide; and
about 35 wt. % to about 65 wt. % of the second polysaccharide.

14. The chromogenic absorbent material of claim 1, wherein the absorptive material further comprises a superabsorbent polymer (SAP).

15. The chromogenic absorbent material of claim 1, wherein the chromogenic absorbent material is provided with pores having an equivalent diameter greater than about 20 μm.

16. The chromogenic absorbent material of claim 1, having a free swelling capacity greater than about 900%.

17. The chromogenic absorbent material of claim 1, wherein the density is about 0.25 g/cm3 to about 0.35 g/cm3.

18. The chromogenic absorbent material of claim 1, wherein the chromogenic absorbent material is a porous material having an effective porosity of about 0.5 mL/g to about 2.0 mL/g.

19. The chromogenic absorbent material of claim 18, wherein the effective porosity is about 0.6 mL/g to about 1.5 mL/g.

20. A chromogenic absorbent material for detecting a detectable substance in an animal excretion, the chromogenic absorbent material comprising:
a trigger agent;
a chromogenic indicator oxidizable into a colored and/or fluorescent substance in the presence of the trigger agent and the detectable substance; and
an absorptive material which is porous, for absorbing the animal excretion, the absorptive material comprising a water-absorbing polysaccharide;

wherein the chromogenic absorbent material is provided with pores having an equivalent diameter greater than about 20 μm.

21. A chromogenic absorbent material for detecting a detectable substance in an animal excretion, the chromogenic absorbent material comprising:
a trigger agent;
a chromogenic indicator oxidizable into a colored and/or fluorescent substance in the presence of the trigger agent and the detectable substance; and
an absorptive material which is porous, for absorbing the animal excretion, the absorptive material comprising a water-absorbing polysaccharide;
wherein the chromogenic absorbent material has a free swelling capacity greater than about 900%.

22. A chromogenic absorbent material for detecting a detectable substance in an animal excretion, the chromogenic absorbent material comprising:
a trigger agent;
a chromogenic indicator oxidizable into a colored and/or fluorescent substance in the presence of the trigger agent and the detectable substance; and
an absorptive material which is porous, for absorbing the animal excretion, the absorptive material comprising a water-absorbing polysaccharide;
wherein the chromogenic absorbent material is a porous material having an effective porosity of about 0.5 mL/g to about 2.0 mL/g.

* * * * *